(12) United States Patent
Bantel et al.

(10) Patent No.: US 11,028,178 B2
(45) Date of Patent: Jun. 8, 2021

(54) METHOD OF TREATING NONALCOHOLIC STEATOHEPATITIS BY ADMINISTERING AN ANTAGONIST HUMAN TUMOR NECROSIS FACTOR RECEPTOR 1 (HUTNFR1) ANTIBODY

(71) Applicant: BALIOPHARM AG, Basel (CH)

(72) Inventors: Heike Bantel, Hannover (DE); Klaus Pfizenmaier, Tiefenbronn (DE); Andreas Herrmann, Pfeffingen (CH)

(73) Assignee: BALIOPHARMA AG, Basel (CH)

( * ) Notice: Subject to any disclaimer, the term of this patent is extended or adjusted under 35 U.S.C. 154(b) by 0 days.

(21) Appl. No.: 16/766,841

(22) PCT Filed: Nov. 27, 2018

(86) PCT No.: PCT/EP2018/082634
§ 371 (c)(1),
(2) Date: May 26, 2020

(87) PCT Pub. No.: WO2019/102023
PCT Pub. Date: May 31, 2019

(65) Prior Publication Data
US 2020/0299396 A1    Sep. 24, 2020

(30) Foreign Application Priority Data
Nov. 27, 2017 (EP) .................................. 17203853

(51) Int. Cl.
| | | |
|---|---|---|
| *C07K 16/28* | (2006.01) | |
| *A61P 1/16* | (2006.01) | |
| *A61P 3/00* | (2006.01) | |
| *A61K 39/395* | (2006.01) | |
| *A61K 39/00* | (2006.01) | |
| *A61K 45/06* | (2006.01) | |

(52) U.S. Cl.
CPC ...... *C07K 16/2878* (2013.01); *A61K 39/3955* (2013.01); *A61P 1/16* (2018.01); *A61P 3/00* (2018.01); *A61K 45/06* (2013.01); *A61K 2039/505* (2013.01); *A61K 2039/545* (2013.01); *C07K 2317/565* (2013.01); *C07K 2317/76* (2013.01)

(58) Field of Classification Search
CPC ............ C07K 16/2878; C07K 2317/24; C07K 2317/565; C07K 2317/76; A61K 39/3955; A61K 45/06; A61K 2039/505; A61K 2039/545; A61P 1/16; A61P 3/00
See application file for complete search history.

(56) References Cited

U.S. PATENT DOCUMENTS 5,736,138 A    4/1998    Pfizenmaier et al.

FOREIGN PATENT DOCUMENTS

| WO | 2007/058894 A2 | 5/2007 |
| WO | 2008/113515 A2 | 9/2008 |
| WO | 2012/035141 A1 | 3/2012 |
| WO | 2017/174586 A1 | 10/2017 |

OTHER PUBLICATIONS

Paul, WE (1993) Fundamental Immunology, 3rd ed. Raven Press, NY, Chap. 9, pp. 292-295.*
RudikoffS, et al. (1982) Proc. Natl. Acad. Sci. USA, 79:1979-1983.*
Colman, PM (1994) Research in Immunology, Elsevier, NY, 145(1):33-36.*
Branschadel M, et al. (Mar. 2010) Cell Signal. 22(3):404-414. (doi: 10.1016/j.cellsig.2009.10.011).*
Invivogen (2011) "Engineered Fc Regions". 2 pages, (https://www.invivogen.com/review-engineered-pfuse-chig—accessed Feb. 13, 2021).*
Li J, et al. (2017) Journal of Nutritional Biochemistry. 41:34-41. (http://dx.doi.org/10.1016/j.jnutbio.2016.12.007).*
Aparicio-Vergara, Marcela, et al. "Tumor necrosis factor receptor 1 gain-of-function mutation aggravates nonalcoholic fatty liver disease but does not cause insulin resistance in a murine model." Hepatology 57.2 (2013): 566-576.
Armour, Kathryn L., et al. "Recombinant human IgG molecules lacking Fcγ receptor I binding and monocyte triggering activities." European journal of immunology 29.8 (1999): 2613-2624.
Berger, Verena, et al. "An anti-TNFR1 scFv-HSA fusion protein as selective antagonist of TNF action." Protein Engineering, Design & Selection 26.10 (2013): 581-587.
Brader, Mark L., et al. "Examination of thermal unfolding and aggregation profiles of a series of developable therapeutic monoclonal antibodies." Molecular pharmaceutics 12.4 (2015): 1005-1017.
Brodeur B. R. et al., 1987, Monoclonal Antibody Production Techniques and Applications, (Marcel Dekker, Inc., New York), pp. 51-63.
Cubero, F. J., et al. "TNFR1 determines progression of chronic liver injury in the IKK γ/Nemo genetic model." Cell Death & Differentiation 20.11 (2013): 1580-1592.
Dong, Yun, et al. "Essential protective role of tumor necrosis factor receptor 2 in neurodegeneration." Proceedings of the National Academy of Sciences 113.43 (2016): 12304-12309.
Feagins, Linda A., et al. "Nonalcoholic fatty liver disease: a potential consequence of tumor necrosis factor-inhibitor therapy." European journal of gastroenterology & hepatology 27.10 (2015): 1154.
Gautheron, Jérémie, Mihael Vucur, and Tom Luedde. "Necroptosis in nonalcoholic steatohepatitis." Cellular and molecular gastroenterology and hepatology 1.3 (2015): 264-265.

(Continued)

*Primary Examiner* — Robert S Landsman
(74) *Attorney, Agent, or Firm* — Meunier Carlin & Curfman LLC

(57) ABSTRACT

An antibody specifically recognizing human tumor necrosis factor 1 (hu TNFR1), for use in treating nonalcoholic steatohepatitis (NASH) and disease conditions associated thereto.

16 Claims, 13 Drawing Sheets

Figure 1:
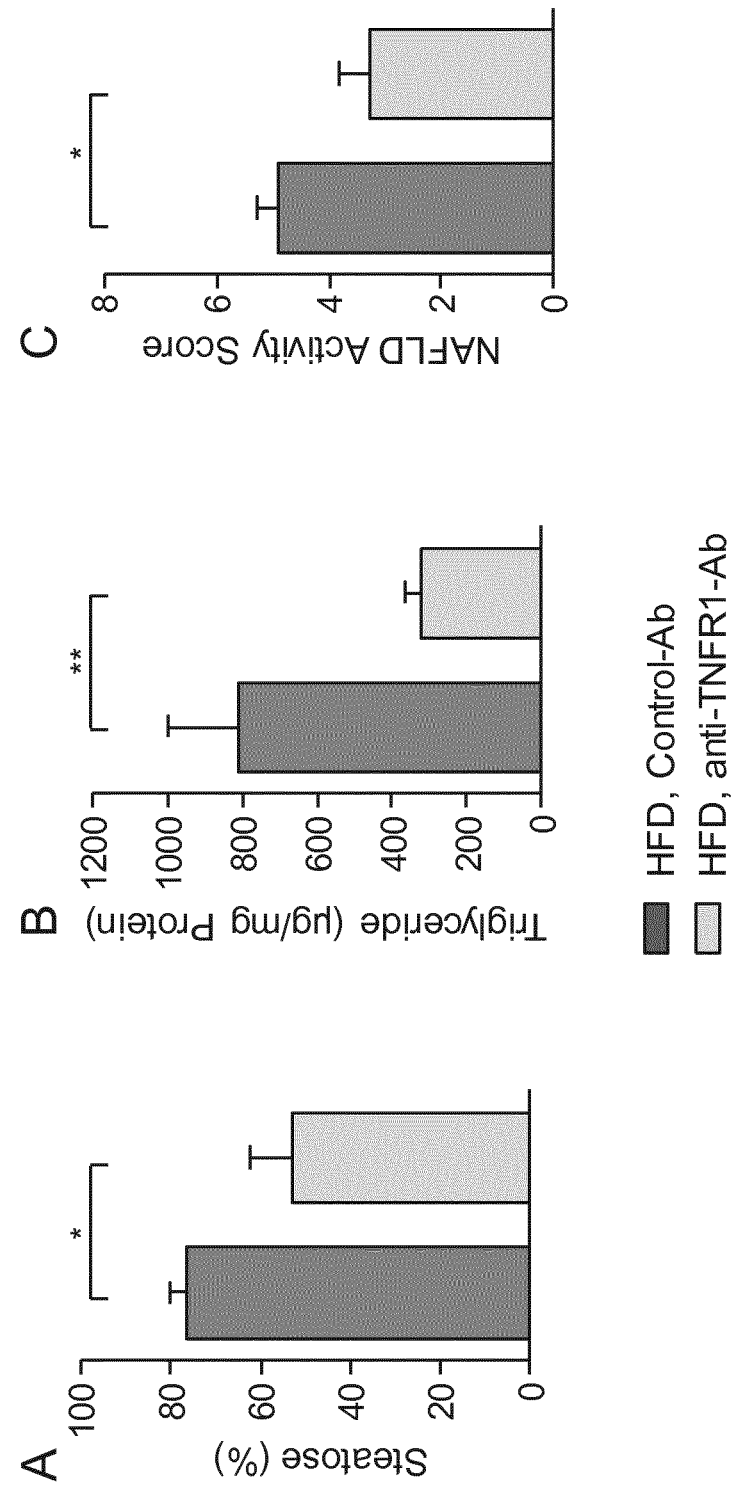

Specification includes a Sequence Listing.

(56) References Cited

OTHER PUBLICATIONS

Gu, Jinming, et al. "Identification of anti-EGFR and anti-ErbB3 dual variable domains immunoglobulin (DVD-Ig) proteins with unique activities." PLoS One 10.5 (2015): e0124135.

Kleiner, David E., et al. "Design and validation of a histological scoring system for nonalcoholic fatty liver disease." Hepatology 41.6 (2005): 1313-1321.

Kohli, Rohit, et al. "High-fructose, medium chain trans fat diet induces liver fibrosis and elevates plasma coenzyme Q9 in a novel murine model of obesity and nonalcoholic steatohepatitis." Hepatology 52.3 (2010): 934-944.

Kozbor, Danuta, et al. "A human hybrid myeloma for production of human monoclonal antibodies." The Journal of Immunology 133.6 (1984): 3001-3005.

Köhler, Georges, and Cesar Milstein. "Continuous cultures of fused cells secreting antibody of predefined specificity." nature 256.5517 (1975): 495-497.

Martin, Nicolas, et al. "Prevention of thermally induced aggregation of IgG antibodies by noncovalent interaction with poly (acrylate) derivatives." Biomacromolecules 15.8 (2014): 2952-2962.

Moosmayer, D., et al. "A single-chain TNF receptor antagonist is an effective inhibitor of TNF mediated cytotoxicity." Therapeutic immunology 2.1 (1995): 31-40.

Richter, Fabian, et al. "Antagonistic TNF receptor one-specific antibody (ATROSAB): receptor binding and in vitro bioactivity." PloS one 8.8 (2013): e72156, 1-13.

Schindelin, Johannes, et al. "Fiji: an open-source platform for biological-image analysis." Nature methods 9.7 (2012): 676-682.

Tomita, Kengo, et al. "Tumour necrosis factor α signalling through activation of Kupffer cells plays an essential role in liver fibrosis of non-alcoholic steatohepatitis in mice." Gut 55.3 (2006): 415-424.

Wark, Kim L., and Peter J. Hudson. "Latest technologies for the enhancement of antibody affinity." Advanced drug delivery reviews 58.5-6 (2006): 657-670.

Yaron Ilan, 2014, Abstract, XP055459107 "A novel method for anti-TNF based-oral immunotherapy: Oral administration of a plant cell-expressed recombinant anti-TNF fusion protein for treating of fatty liver disease."

Zettlitz, Kirstin A., et al. "ATROSAB, a humanized antagonistic anti-tumor necrosis factor receptor one-specific antibody." MAbs. 2010, vol. 2. No. 6. 639-647.

Extended European Search Report issued for Application No. 17203853, dated Mar. 29, 2018.

International Search Report issued for Application No. PCT/EP2018/082634, dated Jan. 28, 2019.

International Preliminary Report on Patentability and Written Opinion issued for Application No. PCT/EP2018/082634, dated Jun. 2, 2020.

\* cited by examiner

Fig. 2
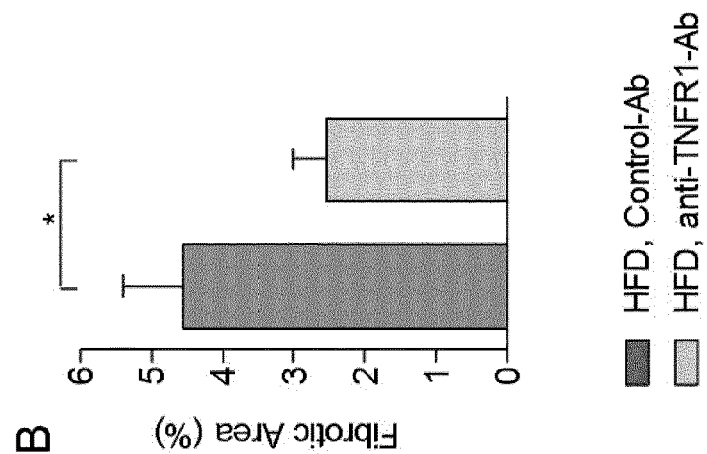
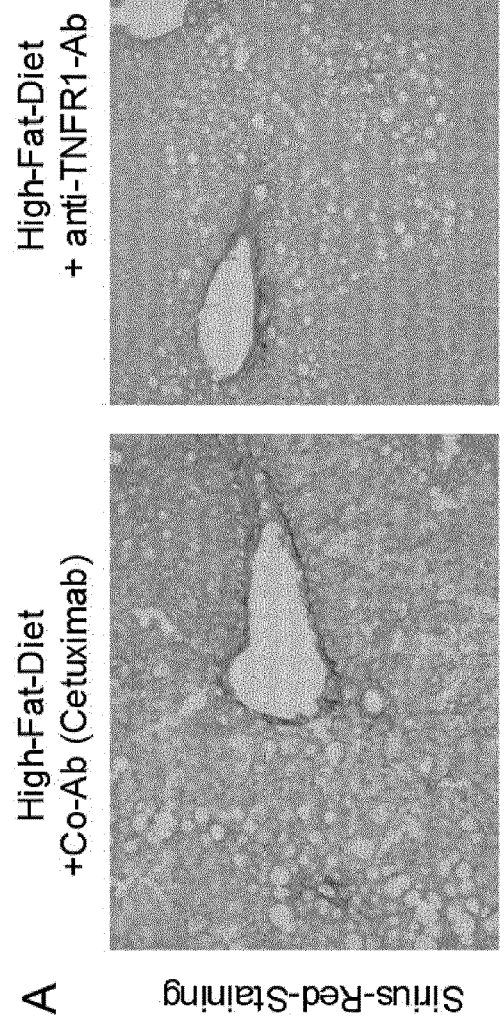

Fig. 5:

SEQ ID NO:1:VH-CDR1
DFYIN

SEQ ID NO:2: VH-CDR2
EIXPXXGXAXYNXKFKA
wherein
X at position 3 is any of Y or V;
X at position 5 is any of Y, T, S or G;
X at position 6 is any of S or Q;
X at position 8 is any of H or E;
X at position 10 is any of Y or K;
X at position 13 is any of E or D.

SEQ ID NO:3: VH-CDR3
WDFLDY

SEQ ID NO:4: VL-CDR1
RSSQSLLHSNGNTYLH

SEQ ID NO:5: VL-CDR2
TVSNRFS

SEQ ID NO:6: VL-CDR3
SQXTHVPYT
wherein X at position 3 is any of S or G

SEQ ID NO:7: VH of IgG13.7/ Fab13.7
HVQLVQSGAEVKKPGSSVKVSCKASGYTFTDFYINWVRQAPGQGLEWIGEIVPSQG
EAKYNDKFKARVTITADKSTSTAYMELSSLRSEDTAVYYCARWDFLDYWGQGTTVTV
SS

SEQ ID NO:8: VL of IgG13.7/ Fab13.7
DVQMTQSPSSLSASVGDRVTITCRSSQSLLHSNGNTYLHWYQQKPGKAPKLLIYTVS
NRFSGVPSRFSGSGSGTDFTLTISSLQPEDFATYYCSQSTHVPYTFGGGTKVEIKRTV
AA

SEQ ID NO:9: VH of ATROSAB/ IZI06.1
QVQLVQSGAEVKKPGSSVKVSCKASGYTFTDFYINWVRQAPGQGLEWIGEIYPYSG
HAYYNEKFKARVTITADKSTSTAYMELSSLRSEDTAVYYCARWDFLDYWGQGTTVTV
SS

Fig. 5 (continued):

SEQ ID NO:10: VL of ATROSAB/ IZI06.1
DIVMTQSPLSLPVTPGEPASISCRSSQSLLHSNGNTYLHWYLQKPGQSPQLLIYTVSN
RFSGVPDRFSGSGSGTDFTLKISRVEAEDVGVYYCSQSTHVPYTFGGGTKVEIKR

SEQ ID NO:11: (Fab13.7 Heavy chain [bold = VH])
**HVQLVQSGAEVKKPGSSVKVSCKASGYTFTDFYINWVRQAPGQGLEWIGEIVPSQG
EAKYNDKFKARVTITADKSTSTAYMELSSLRSEDTAVYYCARWDFLDYWGQGTTVT
VSS**ASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSC SEQ ID NO:12: (Fab13.7 Light chain [bold = VL])
**DVQMTQSPSSLSASVGDRVTITCRSSQSLLHSNGNTYLHWYQQKPGKAPKLLIYTV
SNRFSGVPSRFSGSGSGTDFTLTISSLQPEDFATYYCSQSTHVPYTFGGGTKVEIKR
TVAA**PSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC SEQ ID NO:13: *VL1C (VL13.7-CH2-CH31; VL and CH1 containing chain):*
DVQMTQSPSSLSASVGDRVTITCRSSQSLLHSNGNTYLHWYQQKPGKAPKLLIYTV
SNRFSGVPSRFSGSGSGTDFTLTISSLQPEDFATYYCSQSTHVPYTFGGGTKVEIKG
TGGGSGPSVFLFPPKPKDTLMISRTPEVTCVVVDVSHEDPEVKFNWYVDGVEVHNA
KTKPREEQYNSTYRVVSVLTVLHQDWLNGKEYKCKVSNKGLPSSIEKTISKAKGQP
REPSVFPLAPSSKSTSGGTAALGCLVKDYFPSDIAVEWESGALTSGVHTFPAVLQS
SGLYSLSSVVTVPSSSLGTQTYSCSVMHEALHNHYTQKSVEPKSC VL1C detailed:

SEQ ID NO:14: VL13.7
DVQMTQSPSSLSASVGDRVTITCRSSQSLLHSNGNTYLHWYQQKPGKAPKLLIYTVS
NRFSGVPSRFSGSGSGTDFTLTISSLQPEDFATYYCSQSTHVPYTFGGGTKVEIK

SEQ ID NO:15: Linker
GTGGGSG

SEQ ID NO:16: CH2
PSVFLFPPKPKDTLMISRTPEVTCVVVDVSHEDPEVKFNWYVDGVEVHNAKTKPREE
QYNSTYRVVSVLTVLHQDWLNGKEYKCKVSNKGLPSSIEKTISKAK

SEQ ID NO:17: CH31
GQPREPSVFPLAPSSKSTSGGTAALGCLVKDYFPSDIAVEWESGALTSGVHTFPAVL
QSSGLYSLSSVVTVPSSSLGTQTYSCSVMHEALHNHYTQKSVEPKSC

SEQ ID NO:18: *VHkC (VH13.7-CH2-CH3kappa; VH and CLk containing chain):*
**HVQLVQSGAEVKKPGSSVKVSCKASGYTFTDFYINWVRQAPGQGLEWIGEIVPSQG
EAKYNDKFKARVTITADKSTSTAYMELSSLRSEDTAVYYCARWDFLDYWGQGTTVT
VSS**GTGGGSGPSVFLFPPKPKDTLMISRTPEVTCVVVDVSHEDPEVKFNWYVDGVE
VHNAKTKPREEQYNSTYRVVSVLTVLHQDWLNGKEYKCKVSNKGLPSSIEKTISKA
KGQPREPSVFIFPPSDEQLKSGTASVVCLVNNFYPRDIAVEWEVDNALQSGNSQES
VTEQDSKDSTYSLSSTLTLSKADYEKHKVYSCSVMHEALHNHYTQKSFNRGEC Fig. 5 (continued):

VHkC detailed:

SEQ ID NO:19: VH13.7
HVQLVQSGAEVKKPGSSVKVSCKASGYTFTDFYINWVRQAPGQGLEWIGEIVPSQG
EAKYNDKFKARVTITADKSTSTAYMELSSLRSEDTAVYYCARWDFLDYWGQGTTVTV
SS

SEQ ID NO:15: Linker
GTGGGSG

SEQ ID NO:16: CH2
PSVFLFPPKPKDTLMISRTPEVTCVVVDVSHEDPEVKFNWYVDGVEVHNAKTKPREE
QYNSTYRVVSVLTVLHQDWLNGKEYKCKVSNKGLPSSIEKTISKAK

SEQ ID NO:20: CH3k
GQPREPSVFIFPPSDEQLKSGTASVVCLVNNFYPRDIAVEWEVDNALQSGNSQESVT
EQDSKDSTYSLSSTLTLSKADYEKHKVYSCSVMHEALHNHYTQKSFNRGEC

SEQ ID NO:21: _VL1C (VL13.7-CH2-CH31; VL and CH1 containing chain):_
gatgtgcagatgacccagagccccagcagcctgtctgccagcgtgggcgacagagtgaccatcacctgtcggagcag
ccagagcctgctgcacagcaacggcaacacctacctgcattggtatcagcagaagcccggcaaggccccccaagctg
ctgatctacaccgtgtccaacagattcagcggcgtgccctctagattctccggctctggcagcggcaccgacttcaccctg
accatctctagcctgcagccccgaggacttcgccacctactactgcagccagtccacccacgtgccgtatacctttggcgg
aggcaccaaggtggaaatcaaaggtaccggcggaggatctggccctagcgtgttcctgttccccccaaagcccaagg
acaccctgatgatctcccggaccccgaagtgacctgcgtggtggtggatgtgtcccacgaggaccctgaagtgaagttt
aattggtacgtggacggcgtggaagtgcataacgccaagaccaagcccagagaggaacagtacaacagcacctac
cgggtggtgtccgtgctgaccgtgctgcaccaggactggctgaacggcaaagagtacaagtgcaaggtgtccaacaa
gggcctgcccagcagcatcgagaaaaccatcagcaaggccaagggccagcctcgggaaccctccgtgtttcctctgg
cccctagcagcaagagcacctctggcggaacagccgccctgggctgcctcgtgaaggactacttccccagcgacattg
ccgtggaatgggagtctggcgccctgaccagcggagtgcatacctttccagcagtgctccagagcagcggcctgtaca
gcctgagcagcgtcgtgacagtgcccagctctagcctgggcacccagacctactcttgcagcgtgatgcacgaggccct
gcacaaccactacacccagaaaagcgtggaacccaagagctgc SEQ ID NO:22: _VHkC (VH13.7-CH2-CH3kappa; VH and CLk containing chain):_
cacgtgcagctggtgcagtctggcgccgaagtgaagaaacccggcagcagcgtgaaggtgtcctgcaaggccagcg
gctacaccttcaccgacttctacatcaactgggtgcgccaggctccaggacagggcctggaatggatcggcgagatcgt
gcctagccagggcgaggccaagtacaacgacaagttcaaggccagagtgaccatcaccgccgacaagagcacca
gcaccgcctacatggaactgagcagcctgcggagcgaggacaccgccgtgtactactgcgccagatgggacttcctg
gactactggggccagggcaccaccgtgacagtctcgagcggtaccggcggaggatctggccctagcgtgttcctgttcc
ccccaaagcccaaggacaccctgatgatcagccggaccccgaagtgacctgcgtggtggtggatgtgtcccacgag
gaccctgaagtgaagttcaattggtacgtggacggcgtggaagtgcacaacgccaagaccaagcccagagaggaac
agtacaacagcacctaccgggtggtgtccgtgctgaccgtgctgcaccaggactggctgaacggcaaagagtacaag
tgcaaggtgtccaacaagggcctgcccagcagcatcgagaaaaccatcagcaaggccaagggccagcctcgggaa
cccagcgtgttcatcttcccaccctccgacgagcagctgaagtctggcacagccagcgtcgtgcctcgtgaacaactt
ctaccccagagacattgccgtggaatgggaggtggacaacgccctccagagcggcaacagccaggaaagcgtgac
cgagcaggacagcaaggactccacctacagcctgagcagcaccctgaccctgagcaaggccgactacgagaaac
ataaggtgtacagctgctccgtgatgcacgaggccctgcacaaccactacacccagaagtccttcaaccggggcgagt
gc Fig. 5 (continued):

SEQ ID NO:23
DFYIN

SEQ ID NO:24
EIYPYSGHAYYNEKFKA

SEQ ID NO:25
WDFLDY

SEQ ID NO:26
RSSQSLLHSNGNTYLH

SEQ ID NO:27
TVSNRFS

SEQ ID NO:28
SQSTHVPYT

SEQ ID NO:29:
QVQLVQSGAEVKKPGSSVKVSCKASGYTFTDFYINWVRQAPGQGLEWIGEIYPYSG
HAYYNEKFKARVTITADKSTSTAYMELSSLRSEDTAVYYCARWDFLDYWGQGTTVTV
SS

SEQ ID NO:30:
DIVMTQSPLSLPVTPGEPASISCRSSQSLLHSNGNTYLHWYLQKPGQSPQLLIYTVSN
RFSGVPDRFSGSGSGTDFTLKISRVEAEDVGVYYCSQSTHVPYTFGGGTKVEIKR

SEQ ID NO:31: human IgG1 Fc:
TCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK SEQ ID NO:32: huTNFR1 sequence:
MGLSTVPDLLLPLVLLELLVGIYPSGVIGLVPHLGDREKRDSVCPQGKYIHPQNNSICC
TKCHKGTYLYNDCPGPGQDTDCRECESGSFTASENHLRHCLSCSKCRKEMGQVEIS
SCTVDRDTVCGCRKNQYRHYWSENLFQCFNCSLCLNGTVHLSCQEKQNTVCTCHA
GFFLRENECVSCSNCKKSLECTKLCLPQIENVKGTEDSGTTVLLPLVIFFGLCLLSLLFI
GLMYRYQRWKSKLYSIVCGKSTPEKEGELEGTTTKPLAPNPSFSPTPGFTPTLGFSP
VPSSTFTSSSTYTPGDCPNFAAPRREVAPPYQGADPILATALASDPIPNPLQKWEDSA
HKPQSLDTDDPATLYAVVENVPPLRWKEFVRRLGLSDHEIDRLELQNGRCLREAQYS
MLATWRRRTPRREATLELLGRVLRDMDLLGCLEDIEEALCGPAALPPAPSLLR SEQ ID NO:33: IgG1 hinge region:
DKTHTCPPCPAPELLGG Fig.7:
a)
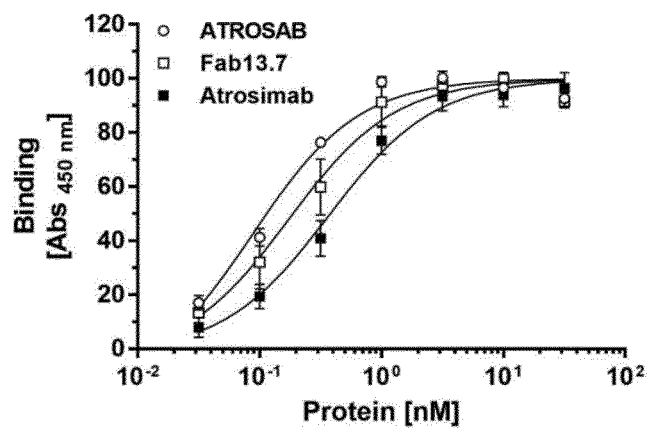
b)
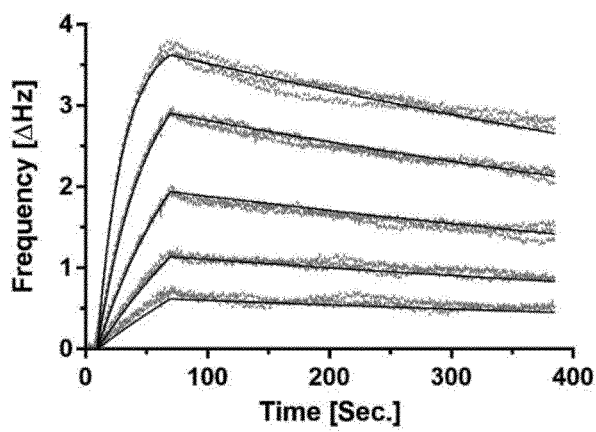
c)
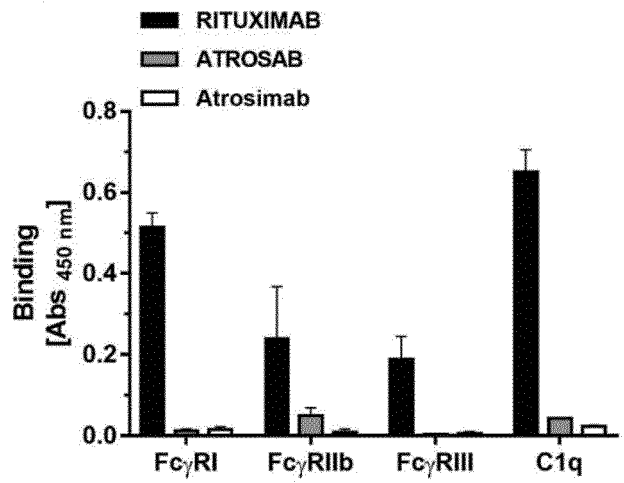

Fig. 9:
a)
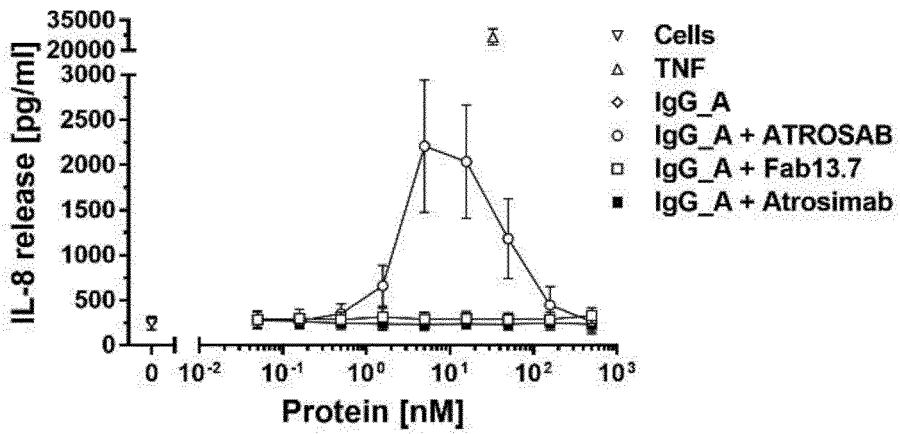
b)
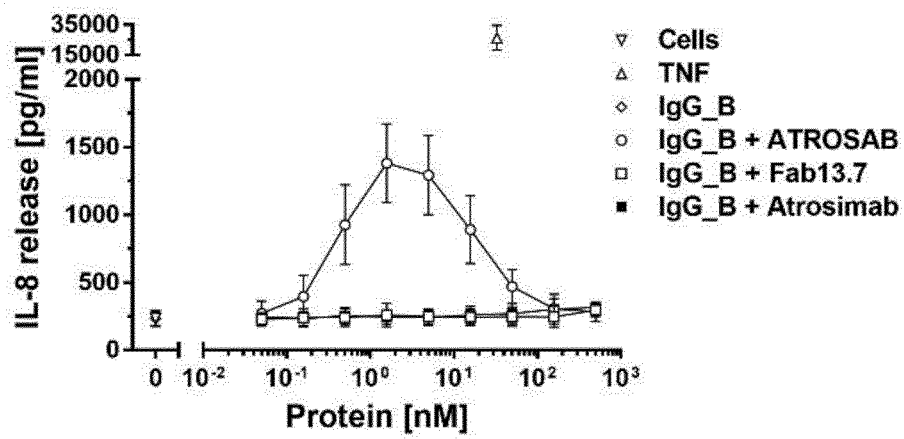
c)
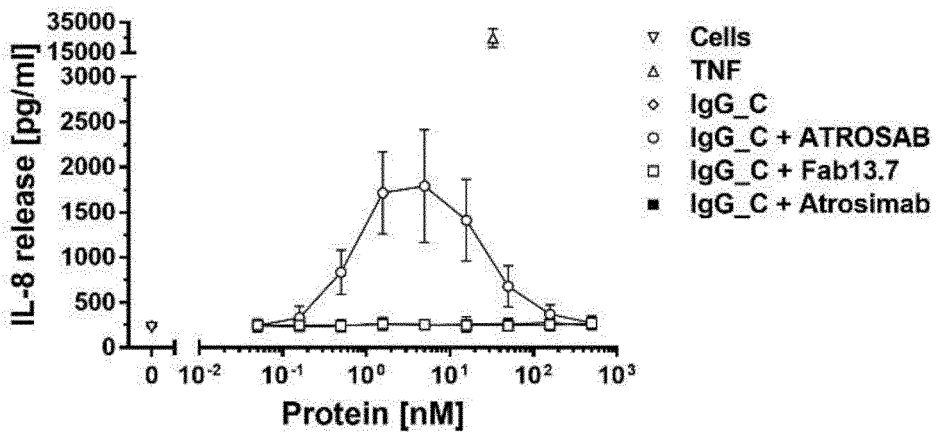

METHOD OF TREATING NONALCOHOLIC STEATOHEPATITIS BY ADMINISTERING AN ANTAGONIST HUMAN TUMOR NECROSIS FACTOR RECEPTOR 1 (HUTNFR1) ANTIBODY

CROSS REFERENCE TO RELATED APPLICATIONS

This is a national phase application filed under 35 U.S.C. § 371 of PCT International Application No. PCT/EP2018/082634, filed on Nov. 27, 2018, entitled "ANTI-huTNFR1 THERAPY OF NONALCOHOLIC STEATOHEPATITIS", which claims priority to, and the benefit of, European Patent Application No. 17203853.1, filed on Nov. 27, 2017, which are incorporated herein by reference in their entireties.

FIELD

The invention relates to a new treatment of nonalcoholic steatohepatitis (NASH) and disease conditions associated thereto.

BACKGROUND

Non-alcoholic fatty liver disease (NAFLD) represents a spectrum of disease occurring in the absence of alcohol abuse and includes non-alcoholic steatohepatitis (NASH). NAFLD shows an increasing incidence in Western countries and critically contributes to the development of hepatocellular carcinoma.

One fundamental step along the sequence from benign liver steatosis toward progressive steatohepatitis is the occurrence of hepatocyte cell death, classified as apoptosis. Necroptosis has emerged as an alternative programmed cell-death pathway, and was found to be activated in livers of NASH patients (Gautheron et al. Cellular and Molecular Gastroenterology and Hepatology 2015, 1:264-266).

Aparicio-Vergara et al. (Hepatology 2013, 57(2):566-576) describe the role of TNFR1 ectodomain shedding in preventing the development of hepatic steatosis or insulin resistance. Inability of TNFR1 shedding did not result in obesity, insulin resistance or hepatic steatosis in mice. However, mice comprising a non-shedding mutation showed a rapid progression towards NASH. Activation of TNFR1 ectodomain shedding was found pivotal in attenuating the progression towards NASH.

Cubero et al. (Cell Death and Differentiation 2013, 20:1580-1592) describe that TNFR1 in hepatocytes and immune cells have different roles in a mode of action in chronic liver disease.

Tomita et al. (Gut 2006, 55:415-424) describe that the enhancement of the TNFa/TNFR mediated signaling pathway may be critically involved in the pathogenesis of liver fibrosis in a NASH animal model.

Yaron Ilan (AASLD Liver Learning. Ilan Y. Nov. 8, 2014; 60709) discloses anti-TNF based oral immunotherapy for treating fatty liver disease. An anti-TNF fusion protein (PRX-106) which binds TNFa was used in a high fat diet mouse model.

Antibodies to TNFR1 were found to have an agonistic potential by inducing a response mimicking the ligand. This response suggests that signal transduction is initiated by aggregation of receptors by binding of the multivalent TNF trimers.

Yet, TNFR1-selective inhibition can be achieved with TNFR1-specific antibodies. For example, a monoclonal murine antibody, H398, and antibody described in U.S. Pat. No. 5,736,138, with selectivity for human TNFR1, showed potent inhibition of TNF-mediated signal transduction and cytotoxicity (Moosmayer et al. 1995, Ther. Immunol. 2:31-40).

A humanized version of H398 is described by WO2008/113515A2.

WO2012035141 discloses an anti-huTNFR1 antibody which is deficient in mediating effector function.

Monovalent anti-huTNFR1 antibodies are described in WO2017174586 A1.

Zettlitz et al. (LandesBioscience 2010, November/December:639-647) describe the generation of a humanized TNFR1-specific antagonistic monoclonal antibody.

Richter et al. (PLOS One 2013, 8(8):1-13) describe using a humanized antagonistic anti-TNFR1 antibody for the selective inhibition of TNFR1 singaling to reduce the pro-inflammatory activity of TNF, while leaving TNFR2 untouched.

Berger et al. (Protein Engineering, Design & Selection 2013, 26(10):581-587) describe an anti-TNFR1 scFv-HAS fusion protein as selective antagonist of TNF action.Feagins et al. (Eur J Gastroenterol Hepatol. 2015, 27(10):1154-1160) describe that patients treated with tumor necrosis factor inhibitors (TNFi) develop non-alcoholic fatty liver disease (NASH or steatosis).

The therapeutic possibilities of treating NASH are limited and restricted to life style modifications, since specific drugs are not available so far. There is thus a need to provide an effective treatment of NASH and disease activities associated therewith.

SUMMARY OF THE INVENTION

It is the object of the invention to provide for an improved treatment of NASH and respective disease conditions.

The object is solved by the subject matter of the invention.

The invention provides for the new medical use of antibodies which specifically recognize human tumor necrosis factor receptor 1 (huTNFR1) for treating patients suffering from NASH and/or particularly any of the disease conditions associated with NASH, among them liver steatosis, NAFLD disease activity (NAS), apoptosis, fibrosis, and high alanine transaminase (ALT) and insulin levels. Therefore, the invention provides for the new medical treatment of patients suffering from NASH and disease conditions associated thereto.

Specifically, the invention provides for an antibody specifically recognizing huTNFR1, for use in treating nonalcoholic steatohepatitis (NASH) and disease conditions associated thereto.

According to a specific aspect, the antibody is an isolated antibody.

According to a specific aspect, the antibody is a monoclonal and/or recombinant antibody.

According to a specific aspect, the antibody specifically recognizes an epitope within the membrane-distal CRD1 and/or subdomain Al of CRD2 of huTNFR1, preferably specifically recognizing an epitope represented by amino acid 1 to 115, or 1 to 70 in the N-terminal region of huTNFR1. Specifically, the sequence of huTNFR1 is identified as SEQ ID NO:32.

According to a specific embodiment, the antibody is a monospecific, bivalent full-length antibody, or an antigen-binding antibody fragment.

According to another specific embodiment, the antibody is a monovalent binder of huTNFR1, comprising only one antigen binding site that has a specificity to bind huTNFR1. Specifically, the antibody monovalently recognizes the huTNFR1.

According to a specific embodiment, the antibody is selected from the "monovalent antibody" group consisting of Fab molecules, scFv molecules, single variable domains, disulfide-stabilized Fv (dsFv), half-IgG1 antibodies, and Fv domains, or a functionally active derivative of any of the foregoing, preferably wherein the antibody construct is coupled to a hydrophilic polymer, such as PEG, and/or fused to a polypeptide, such as human (or mouse) serum albumin, transferrin, albumin-binding domains or peptides, Ig-binding domains or peptides, PEG-mimetic polypeptide extensions, an antibody Fc fragment, an antibody Fc fragment carrying mutations to allow for preferred heterodimerization (over homodimerization), or a functional variant of any of the foregoing polypeptides.

Specifically, the antibody is any of a Fab, scFv, dsFv, or Fv domain, which is fused to an antibody Fc fragment, wherein the Fc consists of a heterodimer of CH2 and CH3 domains, wherein the CH2 and/or CH3 domains carry one or more point mutations which allow preferential heterodimerization over homodimerization. Specifically, one or both of the CH3 domains in the Fc are modified to change the amino acid structure, such as to obtain a Fc containing the heterodimer of the CH3/CH3 domains.

Specifically, the antibody construct comprises Fv domains fused to an antibody Fc region or fragment, with or without further antibody domains, yet, maintaining the monovalent binding structure of the antibody. A specific example refers to a Fab moiety or Fv moiety fused to Fc or modified Fc.

A preferred antibody comprises a heavy and a light chain, wherein the heavy chain consists of a VH domain, a CH2 and a CH3 domain, optionally further including one or more linkers; and the light chain consists of a VL domain, a CH2 and a CH3 domain, optionally further including one or more linkers.

Specific embodiments comprise a human IgG1 Fc wherein the CH2-CH3 domains form a heterodimer through one or more "knobs-into-holes" mutations, e.g.

"knobs" mutations modifying the surface of CH3 beta-sheets, present on one CH3 domain monomer, which is T366W; and "holes" mutations modifying the surface of CH3 beta-sheets, present on the other CH3 domain monomer, which are selected from the group consisting of T366S, L368A, Y407V.

Specifically, the antibody comprises an Fc region which comprises one or more mutations to downmodulate the effector function. According to a specific aspect, the Fc region is glycoengineered to downmodulate the effector function.

According to a specific embodiment, the antibody construct comprises a human or artificial IgG1 Fc region which is a functional variant of a human IgG1 Fc with at least any of 60%, 70%, 80%, 85%, or 90% sequence identity, which is mutated to downmodulate the effector function. Preferably the Fc region comprises a heavy chain with at least one mutation selected from the group consisting of E233P, L234V, L235A, AG236, A327G, A330S and P331S, preferably comprising A327G/A330S/P331S, (Kabat EU index numbering). Preferably at least two of said mutations, more preferably at least three, four, five or all of the six mutations are engineered into the Fc sequence. SEQ ID NO:31 identifies the sequence of human IgG1 Fc Specifically, the antibody is PEGylated, HESylated, or PSAylated.

Specifically, the antibody is pegylated with a PEG of a molecular weight ranging between 5.000 to 150.000 g/mol. Exemplary antibody constructs, such as Fabs, are pegylated with PEG 40.000.

Specifically, the antibody is a half antibody IgG1, characterized by only one Fab part, a hinge region and one Fc part, wherein the hinge region and/or the Fc part (particularly the human IgG1 Fc) comprises one or more mutations to avoid heavy chain dimerization (Gu et al. (2015) PLoS One 10(1):e0116419), e.g. selected from the group consisting of mutations in the hinge region (SEQ ID NO:33): C226S, C229S (EU numbering), and mutations in the Fc part: P395A, F405R, Y407R, K409D (EU numbering).

Specifically, the antibody is a Fv-Fc fusion protein, wherein the Fv consists of a VH/VL domain pair, and wherein the VH is fused to a first CH2-CH3 domain chain via a first hinge/linker region, and the VL is fused to a second CH2-CH3 domain chain via a second hinge/linker region. Preferably the first and second CH2-CH3 domain chains differ from each other in one or more point mutations, such as to allow preferential heterodimerization between the first and second CH2-CH3 domain chains, thereby obtaining a Fv-Fc preparation which is characterized by the Fc heterodimer, e.g. through "knobs-into holes" mutations as indicated above.

Specifically, the antibody comprises a disulfide-stabilized Fv (dsFv), which is characterized by one or more additional (artificial) interdomain disufide bonds. Such disulphide bonds are obtained by introducing one or more additional cysteine residues into either of the VH and VL domains at suitable positions which may be used as a bridge pier of disulphide bonds bridging the VH and VL domains, which disulphide bonds are obtained upon reducing the cysteines. According to specific examples, a disulphide bond may be introduced into the Fv at any of the following positions in VH and corresponding positions in VL: 44C in VH and 100C in VL, 108C in VH and 55C in VL, 106C in VH and 56C in VL, or 101C in VH and 46C in VL.

Specifically, the antibody comprises a) a heavy chain variable domain (VH) comprising the complementarity-determining regions (CDRs):VH-CDR1, VH-CDR2, and VH-CDR3; and b) a light chain variable domain (VL) comprising the CDRs: VL-CDR1, VL-CDR2, and VL-CDR3, wherein i)

VH-CDR1 comprises or consists of SEQ ID NO:1;
VH-CDR2 comprises or consists of SEQ ID NO:2
VH-CDR3 comprises or consists of SEQ ID NO:3
VL-CDR1 comprises or consists of SEQ ID NO:4
VL-CDR2 comprises or consists of SEQ ID NO:5
VL-CDR3 comprises or consists of SEQ ID NO:6;
or ii)

VH-CDR1 comprises or consists of SEQ ID NO:23;
VH-CDR2 comprises or consists of SEQ ID NO:24
VH-CDR3 comprises or consists of SEQ ID NO:25
VL-CDR1 comprises or consists of SEQ ID NO:26
VL-CDR2 comprises or consists of SEQ ID NO:27
VL-CDR3 comprises or consists of SEQ ID NO:28;
wherein numbering is according to the Kabat EU index;
or a functionally active variant of any of i) or ii) above, which comprises 0, 1, or 2 (or up to 1, i.e., 0 or 1) point mutations in each of the CDR sequences, and which specifically recognizes the huTNFR1.

Specifically, the antibody comprises a VH and a VL, wherein
VH-CDR1 comprises or consists of SEQ ID NO:1;
VH-CDR2 comprises or consists of SEQ ID NO:2;
VH-CDR3 comprises or consists of SEQ ID NO:3;
VL-CDR1 comprises or consists of SEQ ID NO:4;
VL-CDR2 comprises or consists of SEQ ID NO:5; and
VL-CDR3 comprises or consists of SEQ ID NO:6;
wherein numbering is according to the Kabat EU index;
or a functionally active variant thereof comprising up to 1 (i.e., 0 or 1) point mutation in any one or more, or in each of the CDR sequences, and which specifically recognizes the huTNFR1.

Specifically, the VH and VL sequences are characterized by the VH- and VL-CDR sequences, wherein
i)
VH-CDR1 comprises or consists of SEQ ID NO:1;
VH-CDR2 comprises or consists of SEQ ID NO: 10, wherein X at position 5 is S;
VH-CDR3 comprises or consists of SEQ ID NO:3;
VL-CDR1 comprises or consists of SEQ ID NO:4;
VL-CDR2 comprises or consists of SEQ ID NO:5; and
VL-CDR3 comprises or consists of SEQ ID NO: 11, wherein X at position 3 is G.
or ii)
VH-CDR1 comprises or consists of SEQ ID NO:1;
VH-CDR2 comprises or consists of SEQ ID NO: 10, wherein X at position 5 is S;
VH-CDR3 comprises or consists of SEQ ID NO:3;
VL-CDR1 comprises or consists of SEQ ID NO:4;
VL-CDR2 comprises or consists of SEQ ID NO:5; and
VL-CDR3 comprises or consists of SEQ ID NO: 11, wherein X at position 3 is S.

Specifically, the antibody comprises a VH sequence comprising or consisting of SEQ ID NO:7 or 9; and a VL sequence comprising or consisting of SEQ ID NO:8 or 10, or a functionally active variant thereof comprising up to 1 point mutation in any one or more, or in each of the CDR sequences, and at least 60% sequence identity in any one or more, or in each of the framework (FR) sequences FR1-4 of VH and VL.

Specific VH/VL combinations comprising an antigen-binding site capable of specifically recognizing and binding to huTNFR1 are any of:
a) a VH sequence comprising or consisting of SEQ ID NO:7; and a VL sequence comprising or consisting of SEQ ID NO:8; or
b) a VL sequence comprising or consisting of SEQ ID NO:9; and a VL sequence comprising or consisting of SEQ ID NO:10.

Specifically, the antibody is a full-length or an antigen-binding antibody fragment comprising or consisting of a Fab, which comprises:
a) a heavy chain (HC) sequence comprising or consisting of SEQ ID NO:11; and
b) a light chain (LC) sequence comprising or consisting of SEQ ID NO:12;
or a functionally active variant thereof comprising up to 1 point mutation in any one or more, or in each of the CDR sequences of the VH and VL domains comprised in the HC and LC, respectively, and at least 60% sequence identity in any one or more, or in each of the FR sequences FR1-4 of VH and VL domains.

Specifically, the antibody comprises:
a) a HC sequence comprising or consisting of SEQ ID NO:18; and
b) a LC sequence comprising or consisting of SEQ ID NO:13;
or a functionally active variant thereof comprising up to 1 point mutation in any one or more, or in each of the CDR sequences of the VH and VL domains comprised in the HC and LC, respectively, and at least 60% sequence identity in any one or more, or in each of the FR sequences FR1-4 of VH and VL domains.

Specific functionally active variants of an antibody comprising the HC identified by SEQ ID NO:18 and the LC identified by SEQ ID NO:13, comprise
a HC consisting of:
a) a VH comprising or consisting of SEQ ID NO:19, or at least the CDR sequences contained in said VH sequence;
b) a linker sequence consisting of 4-10 amino acids e.g., 4, 5, 6, 7, 8, 9, or 10 amino acids, preferably consisting of a number of glycines, serines or threonines, in any combination, such as e.g., the linker consisting of SEQ ID NO:15;
c) a CH2 domain comprising or consisting of SEQ ID NO:16; and
d) a CH3 domain comprising or consisting of SEQ ID NO:20;
and
a LC consisting of
a) a VL comprising or consisting of SEQ ID NO:14, or at least the CDR sequences contained in said VH sequence;
b) a linker sequence consisting of 4-10 amino acids e.g., 4, 5, 6, 7, 8, 9, or 10 amino acids, preferably consisting of a number of glycines, serines or threonines, in any combination, such as e.g., the linker consisting of SEQ ID NO:15;
c) a CH2 domain comprising or consisting of SEQ ID NO:16; and
d) a CH3 domain comprising or consisting of SEQ ID NO:17.

Specifically, such antigen-binding antibody is encoded by one or more nucleic acid molecules comprising
a) the HC coding sequence SEQ ID NO:22; and
b) the LC coding sequence SEQ ID NO:21;
or a functionally active variant thereof comprising up to 1 point mutation in any one or more, or in each of the CDR sequences of the VH and VL domains comprised in the HC and LC, respectively, and at least 60% sequence identity in any one or more, or in each of the FR sequences FR1-4 of VH and VL domains.

According to a specific embodiment, the antibody comprises the antigen-binding site characterized by the following combination of six CDR sequences, which comprises or consists of:
SEQ ID NO:23:VH-CDR1;
SEQ ID NO:24: VH-CDR2;
SEQ ID NO:25: VH-CDR3;
SEQ ID NO:26: VL-CDR1;
SEQ ID NO:27: VL-CDR2; and
SEQ ID NO:28: VL-CDR3;
or a functionally active variant thereof comprising up to 1 point mutation in any one or more, or in each of the CDR sequences, and which specifically recognizes the huTNFR1.

Specifically, the antibody comprises an antigen-binding site incorporated in a VH and VL domain, wherein
a) the VH comprises or consists of SEQ ID NO:29; and
b) the VL comprises or consists of SEQ ID NO:30;
or a functionally active variant thereof comprising 0, 1, or 2 (or up to 1) point mutations in any one or more, or in each of the CDR sequences of the VH and VL domains, and at least 60% sequence identity in any one or more, or in each of the FR sequences FR1-4 of the VH and VL domains.

Specifically, the antibody comprises a VH and a VL domain, wherein at least one of the VH and VL domains is an affinity matured functional variant of a parent domain comprising at least one point mutation in any of the complementary determining region (CDR) sequences, wherein a) the parent VH domain is characterized by the CDR sequences: SEQ ID NO:23, SEQ ID NO:24, and SEQ ID NO:25; and b) the parent VL domain is characterized by the CDR sequences: SEQ ID NO:26, SEQ ID NO:27, and SEQ ID NO:28.

Specifically, said at least one point mutation is in any of SEQ ID NO:24 and/or SEQ ID NO:28.

Specifically, any of the exemplary antibodies (which are those antibody characterized by the sequences provided herein), may be used according to the invention. Likewise, any alternative antibodies which comprise the same antigen-binding site and/or have the same target binding specificity may be used. Particular alternative antibodies are those which are functional variants of the exemplary antibodies, wherein any of the exemplary antibodies can be used as a "parent" to produce a variant, which has the function of specifically recognizing the huTNFR1 target.

Specifically, the antibody is an affinity matured antibody of a parent antibody which is characterized by the sequences provided herein, in particular wherein 1, 2, 3, 4, 5, or 6 of the CDR sequences are functionally active CDR variants comprising up to 1 point mutation compared to the respective CDR in the parent antibody.

In specific embodiments, a functionally active variant antibody comprises only 0, 1, 2, or 3 point mutations in each of the CDR sequences, preferably only 0, 1, or 2 point mutations in each of the CDR sequences, wherein a point mutation is any of a substitution, insertion or deletion of one amino acid.

Any of the functionally active variants of an antibody (a parent antibody) described herein are specifically characterized by the huTNFR1 binding specificity. The functionally active variant may comprise one or more mutant FR sequences, which include one or more, e.g. several point mutations, e.g. up to 2, 3, 4, 5, 6, 7, 8, 9, 10, 11, 12, 13, 14, or 15 point mutations to obtain a variant sequence with at least 60% sequence identity, or at least 70% sequence identity, or at least 80% sequence identity, or at least 90% sequence identity as compared to the respective FR sequence in the parent antibody.

Specifically, the antibody comprises an antigen-binding moiety which is binding huTNFR1 with a $K_D$ of less than $10^{-8}$M or $5\times10^{-9}$M, and a $k_{off}$ of less than $10^{-3}$ s$^{-1}$. The affinity of binding and binding characteristics (association and dissociation) is specifically determined in a standard test for determining monovalent binding, substantially excluding the avidity effects of divalent binding. A standard test is based on the measurement by quartz crystal microbalance (QCM) at physiological temperature (about 37° C., or at 37° C.+/−1° C.). Such affinity measurement is particularly performed in a Fab format. Thus, if the antibody is any other than a Fab molecule, the antigen-binding site is particularly introduced into a respective Fab molecule for affinity measurement by QCM at 37° C. This ensures the comparability of results of affinity measurement of monovalent binders irrespective of avidity effects that could interfere with the affinity measurement. The specifically preferred QCM is performed at moderate receptor density. Specifically, the affinity of the antibody construct binding to the huTNFR1 is determined for the Fab format by QCM at 37° C. and moderate receptor density within the range of 50-100 Hz, e.g. at about 50 Hz, or at 50 Hz+/−10 Hz, or at 50 Hz+/−5 Hz.

Specifically, $K_D$ is less than $4\times10^{-9}$M, or less than $3\times10^{-9}$M, or less than $2\times10^{-9}$M, or less than $10^{-9}$M, or even less than $10^{-10}$M Specifically, the $k_{off}$ is less than $10^{-3}$, or less than $5\times10^{-4}$ s$^{-1}$, or less than $10^{-4}$ s$^{-1}$, or less than $10^{-5}$ s$^{-1}$.

Specifically, the antigen-binding moiety is recognizing the huTNFR1 with a $k_{on}$ of at least $10^{5}$M$^{-1}$s$^{-1}$.

According to a specific aspect, the disease conditions are any of hepatic steatosis, inflamed liver, liver fibrosis (or apoptosis) and hepatocellular carcinoma. Specifically, a NASH patient is treated who is at risk of developing or already suffers from any of the disease conditions. Several indicators of NASH or related disease conditions include the NAFLD disease activity (NAS), and high ALT and insulin serum levels, which can be effectively reduced by the treatment described herein.

Specifically, the patient is also suffering from type II diabetes mellitus, type I diabetes mellitus, pre-diabetes, insulin resistance, or obesity, wherein obesity is defined as the patient having a body mass index of ≥30.

Specifically, the antibody is administered to the patient in an effective amount. Specifically, the amount is effective to antagonize TNFα/huTNFR1 signaling. It is specifically preferred that the antibody is an antagonistic antibody, thereby avoiding the substantial TNFα/TNFR mediated signaling and signal transduction, as measured in a cell-based assay. Any of the antibodies described herein and characterized by the antibody sequences provided herein are particularly understood as being antagonistic antibodies.

According to a specific aspect, the antibody directly inhibits the TNF-huTNFR1 receptor interaction as determined in a cell-based assay, preferably by an assay for inhibition of TNFR1-mediated cell death in Kym-1 cells, or by an assay for inhibition of IL-6 or IL-8 release from HeLa cells or HT1080 cells, respectively. Specifically, in an assay for inhibition of TNFR1-mediated cell death in Kym-1 cells the $IC_{50}$ value is less than $5.0\times10^{-9}$M. Specifically, in an assay for inhibition of IL-6 release from HeLa cells the $IC_{50}$ value is less than $4.0\times10^{-5}$M, or in an assay for inhibition of IL-8 release from HT1080 cells the $10_{50}$ value is less than $2.0\times10^{-5}$M.

According to a specific embodiment, an antibody is used which binds to huTNFR1 by monovalent interaction and has a diminished risk of exhibiting a TNF-mimetic agonistic activity. Specifically preferred are antibodies with a high affinity of binding to TNFR1, and a low off rate, which provides superior inhibition of TNFR1-dependent TNF responses.

Specifically, the antibody described herein is provided in a pharmaceutical preparation comprising the antibody and a pharmaceutically acceptable carrier and/or excipient. Because of the antagonistic properties of the antibody, the pharmaceutical preparation may comprise high antibody concentrations, while avoiding the side effects resulting from agonistic activity.

Specifically, the pharmaceutical preparation is formulated for parenteral use, preferably by intravenous or subcutaneous administration.

Specifically, the antibody described herein has low immunogenicity and may be repeatedly used without formation of inhibitors, such as anti-drug antibodies (ADA).

It has surprisingly turned out that antibodies described herein, particularly monovalent antibodies, can be used for treating patients developing ADA, e.g. which have developed antibodies against immunoglobulin or antibody immunotherapeutics. In the prior art, the presence of such ADA would particularly exclude further immunotherapies with antibodies directed against TNFR1, because ADA have the potential to cross-link the antibodies upon binding the TNFR1 on the cell surface, thereby potentially agonising the TNFR1 signalling. However, antibodies described herein do not (or substantially not) agonise the TNFR1 signaling even in the presence of ADA.

Specifically, the pharmaceutical preparation described herein may be administered to patients who have developed ADA, e.g. ADA against anti-huTNFR1 antibodies or any IgG structures.

Specifically, the effective amount of the antibody is administered to a patient suffering from NASH, to reduce any one or more of a) steatosis, triglyceride content, inflammation, and/or apoptosis in liver tissue;

b) the serum aminotransferase level;

c) insulin-resistance and optionally to improve glucose-tolerance; and/or d) the NAFLD activity score.

Specifically, the antibody is administered to a patient suffering from NASH at a dose ranging from 0.05 mg/kg to 20 mg/kg, preferably 0.2 mg/kg to 6 mg/kg. The amount effective in human beings can be deduced from the therapeutically effective dose in the mouse model described (20 mg/kg). A HED (human equivalent dose) is 1-2 mg/kg.

Preferred antibody doses are, e.g., ranging from 0.5 to 1000 mg, preferably 1-400 mg. If administered subcutaneously, the preferred dosage is ranging from 0.5 to 400 mg.

According to a specific aspect, the antibody is administered to the patient in a therapeutically effective amount by systemic administration, preferably by intravenous infusion or bolus injection.

According to a specific embodiment, the antibody is repeatedly administered to the patient with regular e.g., weekly, i.v. or s.c. injections, at a dose of e.g., 0.5-5 mg/kg, in particular about 2 mg/kg. Frequency and dose of administered drug can be adapted to the disease state and response to therapy.

Specifically, the antibody is administered to a patient suffering from NASH in combination with a dietetic treatment. Antibody treatment may specifically be combined with anti-inflammatory drugs such as NSAP/NSAID, or therapies using a farnesoid X receptor (FXR) agonist, a glucagon-like peptide-1 receptor (GLP1R) agonist, or a peroxisome proliferator-activated receptor (PPAR) agonist.

Unless indicated otherwise, the positions are herein numbered according to the EU index of Kabat. An explanation of the Kabat numbering scheme can be found in Kabat, E A, et al., Sequences of proteins of immunological interest (NIH publication no. 91-3242, 5$^{th}$ edition (1991)).

FIGURES

FIG. 1: B6-huTNFR1-k/i-mice received a high fat diet (HFD) for 32 weeks including a treatment with anti-TNFR1 or control antibody (Ab) for the last 8 weeks. Liver tissues of HFD mice treated with anti-TNFR1-Ab showed a significant reduction of steatosis (A), triglyceride content (B) and NAFLD activity score (C) in liver tissues compared to liver tissues from mice treated with the control antibody. *p<0.05; **p<0.01.

FIG. 2: B6-huTNFR1-k/i-mice received a high fat diet (HFD) for 32 weeks including a treatment with anti-TNFR1 or control antibody (Ab) for the last 8 weeks. Liver tissues of HFD mice treated with anti-TNFR1-Ab showed an improvement of liver fibrosis assessed by Sirius Red staining (A) which was significant compared to liver tissues from mice treated with the control antibody (B). *p<0.05.

Figure 3:
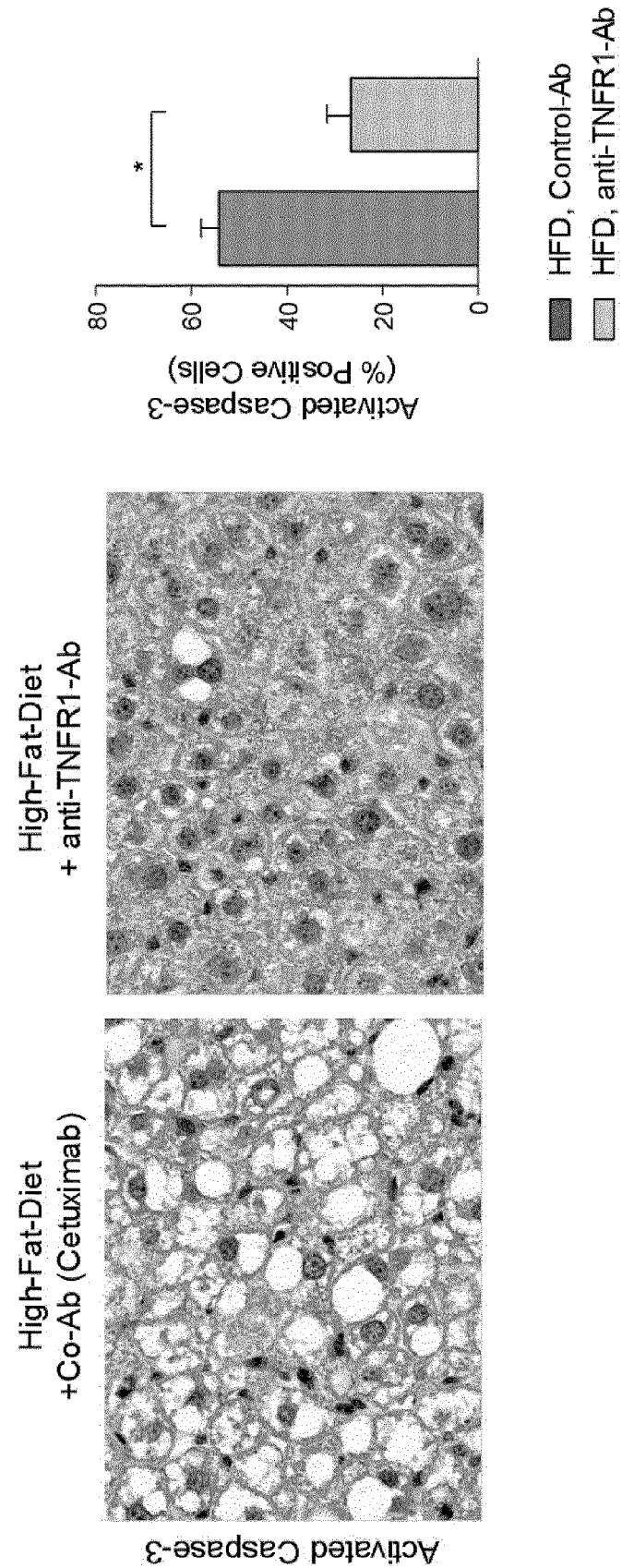

FIG. 3: B6-huTNFR1-k/i-mice received a high fat diet (HFD) for 20 weeks including treatment with anti-TNFR1 or control antibody (Ab) for the last 4 weeks. Compared to control antibody, anti-TNFR1-antibody treatment resulted in a significant reduction of caspase-3 activation in liver tissues. *p<0.05.

Figure 4:
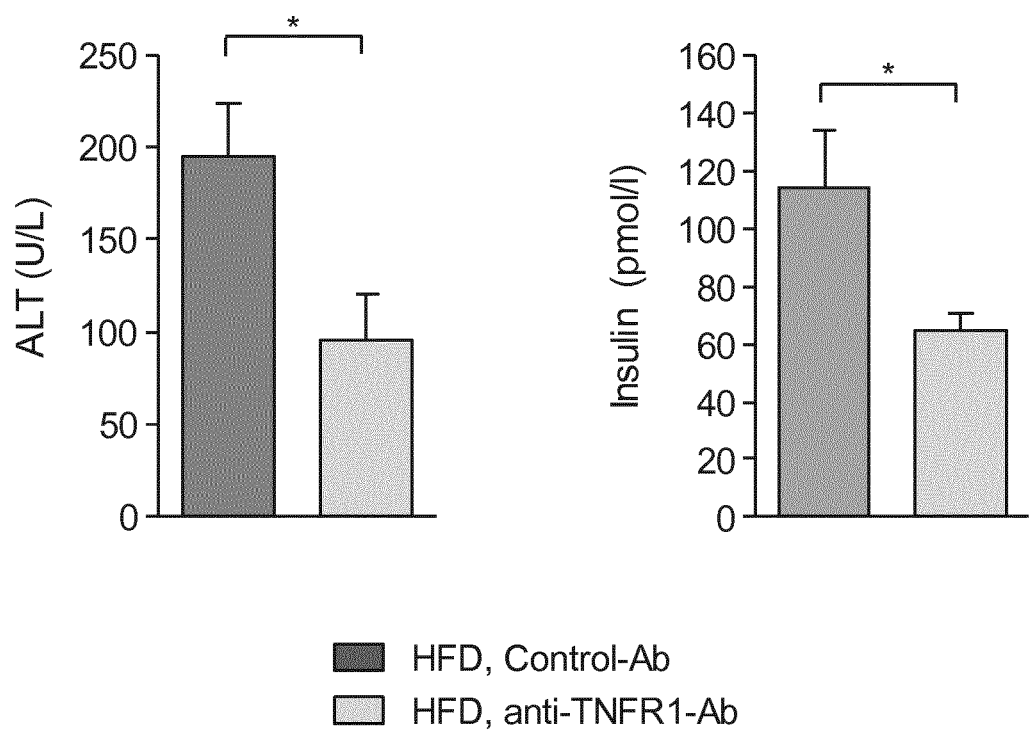

FIG. 4: B6-huTNFR1-k/i-mice received a high fat diet (HFD) for 32 weeks including a treatment with anti-TNFR1 or control antibody (Ab) for the last 8 weeks. Compared to the control antibody, treatment with the anti-TNFR1-Ab resulted in a significant improvement of ALT and insulin serum levels. *p<0.05

Figure 6:
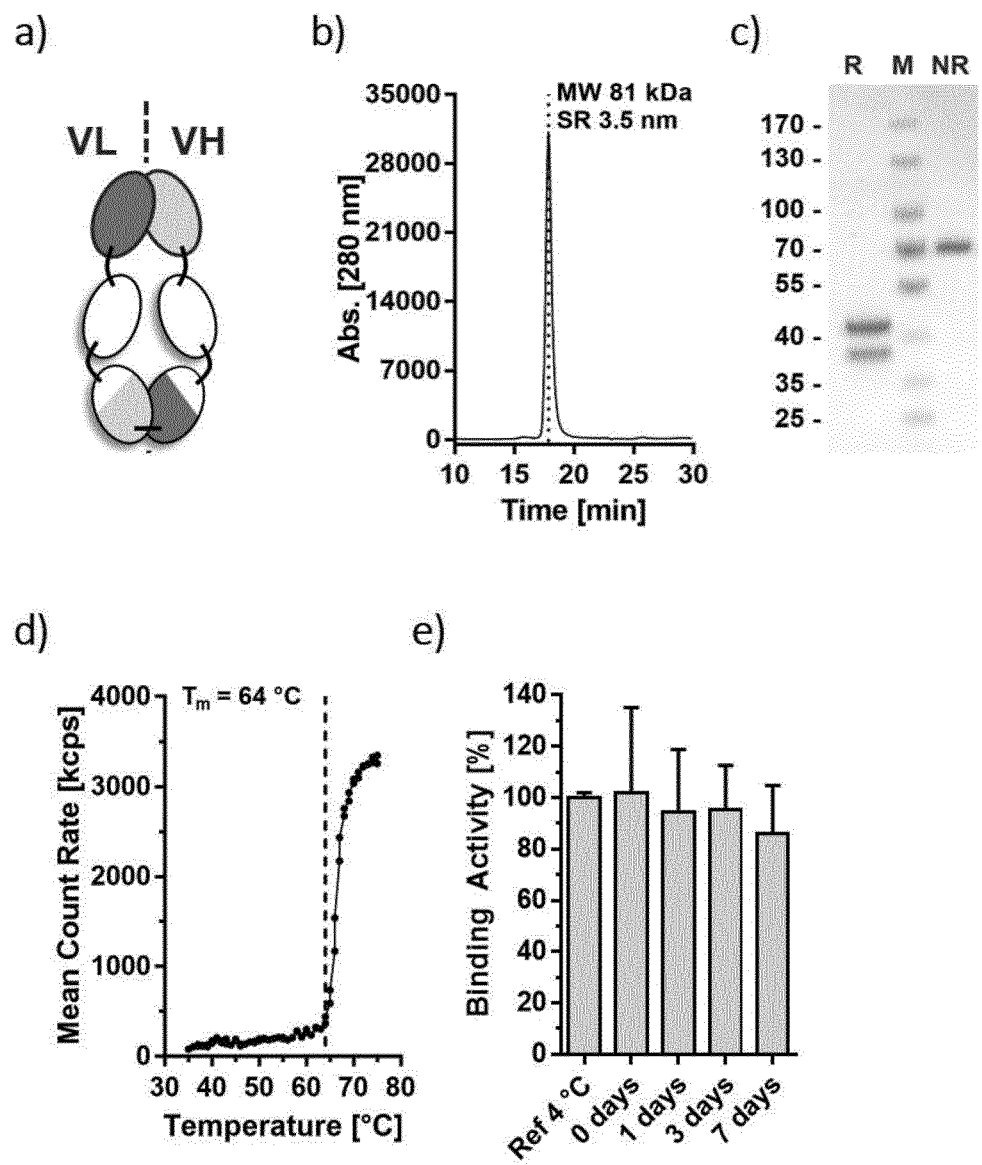

FIG. 5: Sequences
SEQ ID NO:1: VH-CDR1
SEQ ID NO:2: VH-CDR2
SEQ ID NO:3: VH-CDR3
SEQ ID NO:4: VL-CDR1
SEQ ID NO:5: VL-CDR2
SEQ ID NO:6: VL-CDR3
SEQ ID NO:7: VH of IgG13.7/Fab13.7
SEQ ID NO:8: VL of IgG13.7/Fab13.7
SEQ ID NO:9: VH of ATROSAB/IZI06.1
SEQ ID NO:10: VL of ATROSAB/IZI06.1
SEQ ID NO:11: (Fab13.7 Heavy chain [bold=VH])
SEQ ID NO:12: (Fab13.7 Light chain [bold=VL])
SEQ ID NO:13: VL1C (VL13.7-CH2-CH31; VL and CH1 containing chain):
SEQ ID NO:14: VL13.7
SEQ ID NO:15: Linker
SEQ ID NO:16: CH2
SEQ ID NO:17: CH31: CH31 is an interspersed Ig constant domain, that contains mainly residues originating from CH3, but also residues from CH1;
SEQ ID NO:18: VHkC (VH13.7-CH2-CH3kappa; VH and CLk containing chain):
SEQ ID NO:19: VH13.7
SEQ ID NO:20: CH3k
SEQ ID NO:21: VL1C (VL13.7-CH2-CH31; VL and CH1 containing chain):
SEQ ID NO:22: VHkC (VH13.7-CH2-CH3kappa; VH and CLk containing chain):
SEQ ID NO:23: VH-CDR1 of ATROSAB
SEQ ID NO:24: VH-CDR2 of ATROSAB
SEQ ID NO:25: VH-CDR3 of ATROSAB
SEQ ID NO:26: VL-CDR1 of ATROSAB
SEQ ID NO:27: VL-CDR2 of ATROSAB
SEQ ID NO:28: VL-CDR3 of ATROSAB
SEQ ID NO:29: ATROSAB VH
SEQ ID NO:30: ATROSAB VL
SEQ ID NO:31: human IgG1 Fc
SEQ ID NO:32: huTNFR1 sequence:
SEQ ID NO:33: hinge region FIG. 6: Biochemical characterization of Atrosimab (HC: SEQ ID NO:18, LC: SEQ ID NO:13). (a) representative cartoon of the molecular composition of Atrosimab (white: constant Ig domains originating from the Fc; bright grey: VH and sequences originating from CH1; dark grey: VL and sequences originating from $CL_K$). Atrosimab was characterized by SEC (b) TSKgel SuperSW mAb HR, Flow rate 0.5 ml/min, mobile phase Na2HPO4/NaH2PO4) and SDS-PAGE (c) NuPAGETM 4-12% Bis-TRIS Midi Gel) under reducing (R) and non-reducing conditions (NR). M: Marker. (d) Thermal stability of Atrosimab was analyzed by dynamic light scattering and visual interpretation of the obtained data points. Stability of Atrosimab after incubation in human plasma was analyzed by detection of the residual binding activity to human TNFR1 in ELISA (e). Bars represent EC50 values of three individual experiments (mean±SD). One sample incubated in PBS at 4° C. and one sample frozen to −20° C. directly after dilution in human plasma served as controls.

FIG. 7: Antigen binding and interaction with Fc receptors and the C1q Complement protein. Equilibrium binding of Atrosimab to human TNFR1-Fc was analyzed by ELISA ((a) n=3, mean±SD). Fab 13.7 (contains identical VH and VL) and ATROSAB (bivalent version of lower affinity) served as controls. (b) Real-time binding kinetics were recorded by QCM at five concentrations between 128 nM and 4 nM (1:2 dilution steps) using a 1:1 binding algorithm for data analysis. (c) The interaction of immobilized Atrosimab as well as of the two control proteins ATROSAB (silent Fc) and Rituximab (wild-type Fc part) with the human FcγRI, IIb and III and also with the complement protein C1q was analyzed by ELISA (n=2, mean±SD).

Figure 8:
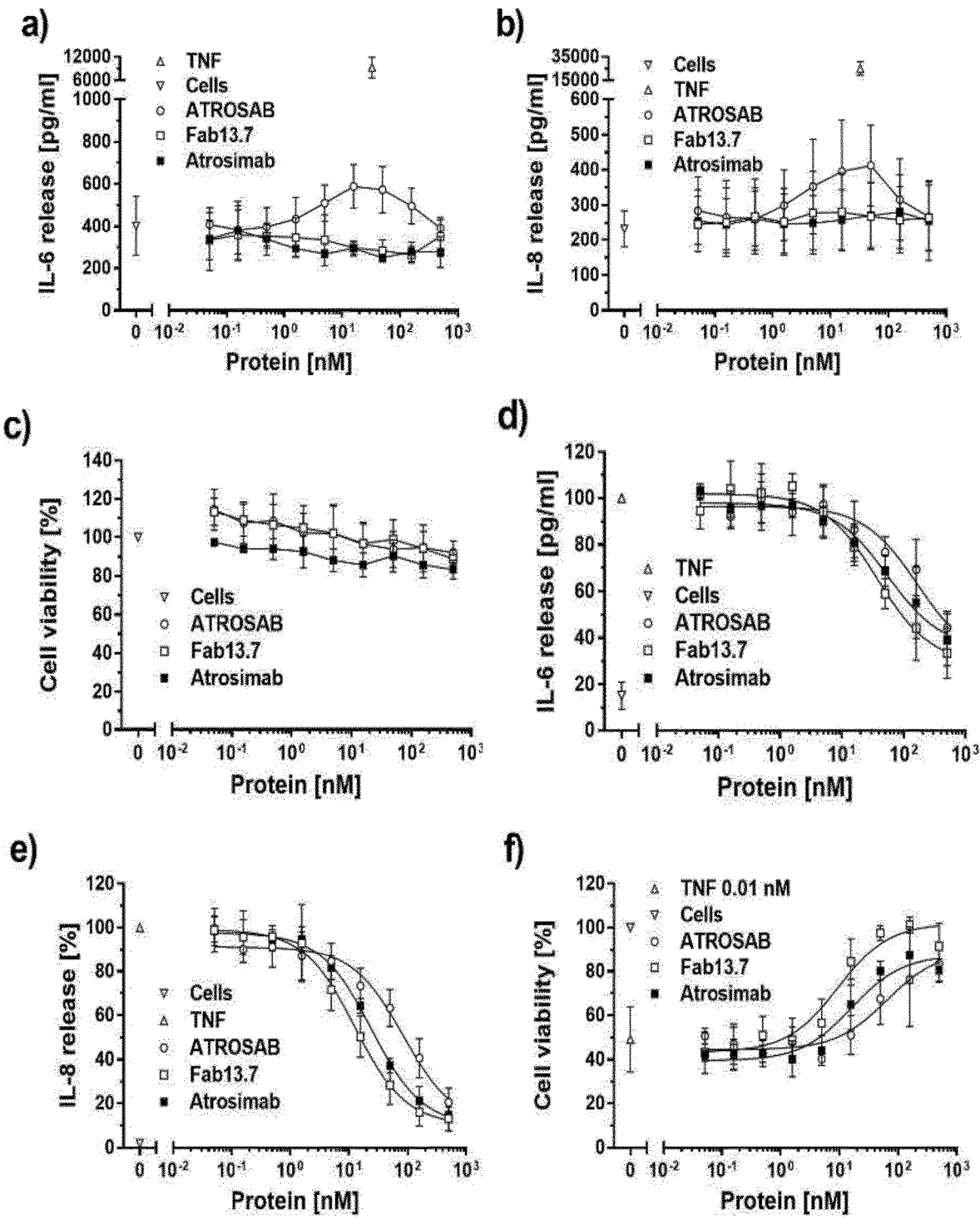

FIG. 8: Antagonistic bioactivity of Atrosimab and lack of agonism. Atrosimab demonstrated a complete lack of agonistic activity in three different in vitro assays: (a) IL 6 release from HeLa cells, (b) IL-8 release from HT1080 cells and in a cell death induction assay using Kym 1 cells (c). The parental Fab 13.7, which demonstrated completely agonistic properties and the bivalent IgG ATROSAB, revealing marginally agonistic effects in (a) and (b), served as control proteins. The same set of proteins was analyzed for the potential to inhibit the activation of TNFR1 on the cellular surface in HeLa, HT1080 and Kym-1 cells as detected by IL-6 release (d), IL-8 release (e) and cell death induction (f), respectively. TNFR1 was activated using 0.1 nM TNF (d and e) or 0.01 nM TNF (f). All graphs represent the mean of three individual Experiments, error bars indicate SD.

FIG. 9: Lack of agonism of Atrosimab in presence of anti-human IgG antibodies. The activation of TNFR1 on the surface of HT1080 cells by Atrosimab in presence of a constant concentration (ca. 15.8 nM) of drug-specific antibodies was analyzed in an IL-8 release assay using three different mouse anti-human IgG sera (a, b and c). The mouse anti-human IgG sera alone, unstimulated cells and TNF (33 nM) served as controls. Shown are mean ±SD of three individual experiments.

Figure 10:
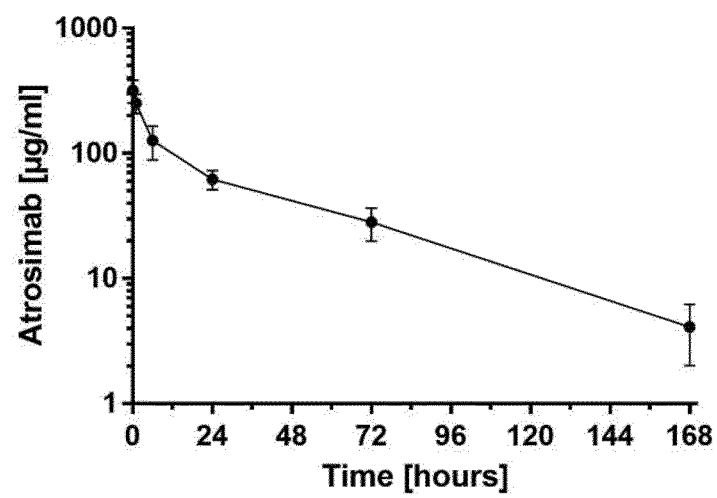

FIG. 10: Pharmacokinetic analysis of Atrosimab. Circulating concentrations of Atrosimab were determined in mouse serum after bolus injection of 400 μg protein in C57BL/6J knock-in mice, which express the extracellular domain of the human TNFR1 connected to the murine transmembrane and intracellular domain instead of the fully murine protein. Intact protein was determined upon binding to human TNFR1-Fc in ELISA. The graph shows mean±SD of five mice.

DETAILED DESCRIPTION OF THE INVENTION

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

The term "antibody" is herein understood to encompass polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The antibody as used herein comprises at least one antigen-binding site, which specifically recognizes huTNFR1 or an epitope of the huTNFR1. Thus, the binding of the antibody to the huTNFR1 receptor can be monovalently through only one huTNFR1-specific binding site per antibody, or bivalently through two huTNFR1-specific binding sites. In particular, the antigen-binding site is of one or two antibody domains. Any of the variable antibody domains alone or in combination, such as a VH domain alone, or a combination of VH and VL domains, may be employed to build the antigen-binding site. Specifically, an antigen-binding site is formed by a combination of CDR sequences. Such combination of CDR sequences is also understood as a CDR binding site, e.g. the antigen binding pocket formed by three CDR sequences of one variable domain, such as the combination of CDRH1, CDRH2, and CDRH3, or the combination of CDRL1, CDRL2, and CDRL3, or else six CDR sequences of two variable domains, such as the combination of CDRH1, CDRH2, CDRH3, CDRL1, CDRL2, and CDRL3. Alternatively, an antigen-binding site may be employed that is derived from a natural ligand to the receptor, or an artificial construct. The CDR sequences referred to herein are designated as follows:

CDRs of a VH domain:
VH-CDR1=CDRH1
VH-CDR2=CDRH2
VH-CDR3=CDRH3
CDRs of a VL domain:
VL-CDR1=CDRL1
VL-CDR2=CDRL2
VL-CDR3=CDRL3

Specifically, a CDR binding site of a single variable antibody domain may be used as antigen-binding site, such as a binding site of domains of the heavy and light chains of the variable region (such as dAb, Fd, VL, Vkappa, Vlambda, VH, VHH), or a binding site of pairs of variable antibody domains, such as a VH/VL pair.

Thus, the antibody comprising a CDR binding site may comprise a single variable antibody domain or a pair of variable binding domains, and optionally further comprise other variable domains, with the same or with a different antigen-binding specificity, e.g., a bispecific or polyspecific antibody, wherein only one antigen-binding site is directed to huTNFR1, and at least one another antigen-binding site is directed to a target different from huTNFR1. Optionally, the antibody construct further comprises constant antibody domains, or combinations of variable and/or constant antibody domains with or without a linking sequence or hinge region.

Specific antibody formats may be used as described herein, e.g., an antibody comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)$_2$, scFv, Fd, Fv, or a full-length antibody, e.g., of an IgG type (e.g., an IgG1, IgG2, IgG3, or IgG4 sub-type), IgA1, IgA2, IgD, IgE, or IgM antibody. The term "full length antibody" can be used to refer to any antibody molecule comprising at least most of the Fc domain and other domains commonly found in a naturally-occurring antibody monomer. This phrase is used herein to emphasize that a particular antibody molecule is not an antibody fragment.

Exemplary monovalent, monospecific binders are Fab, scFv, Fv, domain antibodies, IgG half-antibodies, or monovalent IgGs, such as a one-armed IgG consisting of a complete light chain, one complete heavy chain and an additional Fc chain lacking Fd (Fd=VH–CH1), which may be produced according to the knobs-into holes techniques (or other asymetric Fc parts) so to avoid homodimerization of Fc domains.

Exemplary bi- or polyvalent binders are full-length antibodies of any of the immunoglobulin types, or an antigen-binding antibody fragment of any of the full-length antibodies, which comprises at least two antigen-binding sites e.g., of any one or more of a Fab, F(ab'), (Fab)$_2$, scFv, or Fv.

The term "Fv" is herein understood as the region of variable domains which incorporates the CDR binding site, e.g. of VH, VL or VH/VL. The term "Fv", thus, particulary applies to either VH, VL, or the VH/VL which is the VH domain associated to a VL domain by an interaction between the beta-sheet structure of both variable domains, with or without a linker.

The term "antibody" as used herein shall specifically include antibodies in the isolated form in an antibody preparation, which is substantially free of other antibodies directed against different target antigens or comprising a different structural arrangement of antibody domains. Still, an isolated antibody may be comprised in a combination preparation, containing a combination of the isolated antibody, e.g., with at least one other antibody, such as monoclonal antibodies or antibody fragments having different specificities.

The term "antibody" shall apply to antibodies of animal origin, including human species, such as mammalian, such as human or murine, or avian, such as hen, which term shall particularly include recombinant antibodies that are based on a sequence of animal origin, e.g., human sequences, like in human antibodies. Human antibodies typically comprise variable and constant regions derived from human germline immunoglobulin sequences. Human antibodies are preferably used as described herein, which may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

Yet, the term "antibody" further applies to chimeric antibodies with sequences of origin of different species, such as sequences of murine and human origin, or to humanized antibodies, which contain amino acid sequences of human origin and such of non-human, e.g. rodent origin.

The term "antibody" specifically applies to antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA1, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g., mammalians including human, that comprises genes or sequences from different origin, e.g., murine, chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

Antibody domains may be of native structure or modified by mutagenesis or derivatisation, e.g., to modify the antigen binding properties or any other property, such as stability or functional properties, such as binding to the Fc receptors FcRn and/or Fcgamma receptor (FCGR).

Specific examples refer to non-naturally occurring antibodies which are artificial constructs engineered to specifically recognize the target huTNFR1 by at least one antigen-binding site which comprises one or more artificial CDR sequences, or engineered to produce non-naturally occurring antibody constructs, which have a structure different from any of the naturally-occurring immunoglobulin structures.

Specific examples of an antibody as further described herein are non-naturally occurring, e.g. as provided in a combination preparation with another antibody or active agent, which combination does not occur in nature. Specific further examples refer to an artificial derivative or a variant of a naturally-occurring antibody, or an optimized or affinity-matured variant of a naturally-occurring antibody, or an antibody with a framework-region which is engineered to improve the stability of the antibody. By such optimizing or engineering the antibody comprises one or more synthetic structures or sequences or characteristics, which would not be found in the context of the antibody in nature.

It is understood that the term "antibody" as used herein shall also refer to derivatives of an antibody, in particular functionally active derivatives, herein also referred to as functional variants of antibodies.

Functionally active derivatives are particularly produced by fusion or covalent chemical modification that does not alter the primary amino acid sequence of the antibody itself. Derivatives may e.g., have desired properties including, for example, prolonging the circulation half-life, increasing the stability, reducing the clearance, or altering the immunogenicity. Specific antibody derivatives are understood as any combination of one or more antibody domains or antibodies and/or a fusion protein, in which any domain of the antibody may be fused at any position of one or more other proteins, such as other antibodies, e.g., a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulfide bonding etc. The other substances bound to the antibody may be lipids, carbohydrates, nucleic acids, organic and inorganic molecules or any combination thereof (e.g., PEG, prodrugs or drugs). In a specific embodiment, the antibody is a derivative comprising a drug, e.g., to obtain an antibody-drug conjugate.

The term derivative also includes fragments, variants, analogs or homologs of antibodies, e.g., with a specific glycosylation pattern, e.g., produced by glycoengineering, which are functional and may serve as functional variants, e.g., binding to the specific target.

The term "glycoengineered" with respect to antibody sequences shall refer to glycosylation variants having modified immunogenic properties, ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC). Removal of N-Glycan at N297, e.g., through mutating N297, e.g., to A, or T299 typically results in aglycosylated antibodies with reduced ADCC.

Major differences in antibody glycosylation occur between cell lines, and even minor differences are seen for a given cell line grown under different culture conditions. Expression in bacterial cells typically provides for an aglycosylated antibody.

Antibodies can be devoid of an active Fc moiety, thus, either composed of antibody domains that do not have an FCGR binding site, specifically including any antibody devoid of a chain of CH2 and CH3 domains, or comprising antibody domains lacking Fc effector function, e.g., by modifications to reduce Fc effector functions, in particular to abrogate or reduce ADCC and/or CDC activity. Such modifications may be effected by mutagenesis, e.g., mutations in the FCGR binding site or by derivatives or agents to interfere with ADCC and/or CDC activity of an antibody, so to achieve reduction of Fc effector function or lack of Fc effector function, which is typically understood to refer to Fc effector function of less than 10% of the unmodified (wild-type) antibody, preferably less than 5%, as measured by ADCC and/or CDC activity.

Exemplary antibodies may comprise an Fc fragment or at least part of an Fc fragment, such as to maintain the binding site to FcRn, thereby obtaining an antibody with substantive half-life in vivo.

Yet, the Fc can be modified to obtain reduction of possible ADCC and/or CDC activity, e.g., by a switch of IgG1 to IgG2 subtype or by modifications to reduce binding to the Fc receptor, e.g., by E233P and/or L234V and/or L235A and/or D265G and/or A327Q and/or A330A and/or G236, deletion and/or A327G and/or A330S in a human IgG1 Fc, wherein numbering is according to Kabat [EU-Index].

Further examples refer to a modification to reduce immunogenicity, e.g., by a K. O. glycosylation site, such as N297Q, which provides for an impaired binding to lectin receptor.

It is understood that the term "antibody" also refers to variants of an antibody, including antibodies with functionally active CDR variants of a parent CDR sequence, and functionally active variant antibodies of a parent antibody. For example, functional variants of those antibodies which are characterized by the CDR binding sequences and/or by heavy and light chain sequences provided herein, may be engineered and used as further described herein.

Specifically, an antibody variant of a parent antibody can be produced by engineering at least one of antibody sequences of a parent antibody such as any of the exemplary antibodies provided herein, e.g., where the antibody variant comprises at least 3 CDRs of the heavy chain variable region and optionally further at least 3 CDRs of the light chain variable region, with at least one point mutation in at least one of the CDRs or in the FR regions, or in the constant region of the heavy chain (HC) or light chain (LC), still being functionally active, as measured by the specific binding to the target huTNFR1.

Specifically, the antibody variant is a mutant antibody or antibody fragment, e.g., obtained by mutagenesis methods, in particular to delete, exchange, introduce inserts into a specific antibody amino acid sequence or region or chemically derivatise an amino acid sequence, e.g., in the constant domains to engineer the antibody stability, effector function or half-life, or in the variable domains to improve antigen-binding properties, e.g., by affinity maturation techniques available in the art. Any of the known mutagenesis methods may be employed, including point mutations at desired positions, e.g., obtained by randomization techniques. In some cases positions are chosen randomly, e.g., with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

A point mutation is particularly understood as the engineering of a poly-nucleotide that results in the expression of an amino acid sequence that differs from the non-engineered amino acid sequence in the substitution or exchange, deletion or insertion of one or more single (non-consecutive) or doublets of amino acids for different amino acids.

Specifically, a functionally active variant antibody is produced by modification of a parent antibody or a parent antibody sequence by any one or more of insertion, deletion or substitution of one or more amino acids, or chemical derivatisation of one or more amino acid residues in the amino acid sequence, or nucleotides within the nucleotide sequence, or at either or both of the distal ends of the sequence, e.g., in a CDR sequence the N-terminal and/or C-terminal 1, 2, 3, or 4 amino acids, and/or the centric 1, 2, 3, or 4 amino acids (i.e. in the midst of the CDR sequence), and which modification does not affect, in particular impair, the activity of this sequence. In the case of a binding site having specificity to a selected target antigen, the functionally active variant of an antibody would still have the predetermined binding specificity, or substantially the same biological activity, though this could be changed, e.g., to change the fine specificity to a specific epitope, the affinity, the avidity, the Kon or Koff rate, etc. For example, an affinity matured antibody is specifically understood as a functionally active variant antibody. Hence, the modified CDR sequence in an affinity matured antibody is understood as a functionally active CDR variant.

Affinity maturation is the process by which antibodies with increased affinity for a target antigen are produced. Any one or more methods of preparing and/or using affinity maturation libraries available in the art may be employed in order to generate affinity matured antibodies in accordance with various embodiments of the invention disclosed herein. Exemplary such affinity maturation methods and uses, such as random mutagenesis, bacterial mutator strains passaging, site-directed mutagenesis, mutational hotspots targeting, parsimonious mutagenesis, antibody shuffling, light chain shuffling, heavy chain shuffling, CDR1 and/or CDR1 mutagenesis, and methods of producing and using affinity maturation libraries amenable to implementing methods and uses in accordance with various embodiments of the invention disclosed herein, include, for example, those disclosed in: Wark & Hudson, 2006, Advanced Drug Delivery Reviews 58: 657-670.

With structural changes of an antibody, including amino acid mutagenesis or as a consequence of somatic mutation in immunoglobulin gene segments, variants of a binding site to an antigen are produced and selected for greater affinities. Affinity matured antibodies may exhibit a several logfold greater affinity than a parent antibody. Single parent antibodies may be subject to affinity maturation. Alternatively pools of antibodies with similar binding affinity to the target antigen may be considered as parent structures that are varied to obtain affinity matured single antibodies or affinity matured pools of such antibodies.

The preferred affinity matured variant of an antibody described herein exhibits at least a 2-fold increase in affinity of binding, preferably at least a 5-, preferably at least 10-, preferably at least 50-, or preferably at least 100-fold increase. The affinity maturation may be employed in the course of the selection campaigns employing respective libraries of parent molecules, either with antibodies having medium binding affinity to obtain the antibody described herein. Alternatively, the affinity may be even more increased by affinity maturation of the antibody described herein to obtain the high values corresponding to a $K_D$ of less than $10^{-10}$M, or even less than $10^{-11}$M.

In certain embodiments, binding affinity is determined by an affinity ELISA assay. In certain embodiments binding affinity is determined by a BIAcore, ForteBio or MSD assays. In certain embodiments binding affinity is determined by a kinetic method. In certain embodiments binding affinity is determined by an equilibrium/solution method. In certain embodiments binding affinity is determined by standard quartz crystal microbalance (QCM) measurements, in particular at predetermined conditions, which resemble the physiological conditions (about 37° C., density about 50 Hz).

A specific function of antibodies described herein is the function as an inhibitor (also called antagonist) of the TNF-huTNFR1 interaction. The term "inhibitor" as understood herein is a substance having the capability to a) modulate (e.g., reduce or eliminate) TNFR1 signaling in vitro and/or in vivo, and/or b) to inhibit the TNFR1-mediated cell death in vitro and/or in vivo, and/or c) to inhibit TNF-mediated cellular stimulation to release inflammatory cytokines in vitro and/or in vivo, d) by inhibition of TNFR1 signaling by a different mechanism.

In particular, the antibody as used herein interferes with the binding of one or more molecules TNF to one or more molecules of TNFR1 on the cell surface. For therapeutic applications, without being bound by theory, TNF-huTNFR1 interaction inhibitors can have the capability to inhibit huTNFR1 signaling in the presence of TNF, or huTNFR1 mediated cell death in the presence of TNF, or to inhibit cellular stimulation to release inflammatory cytokines in the presence of TNF.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

Inhibition of the huTNFR1 interaction may lead to a downmodulation of the effects of TNFR1 signaling or signal transduction, as measured ex vivo in a cell-based assay or in vivo, in a dose-dependent way. The functional activity of the antibody described herein is specifically characterized by an inhibitory function which inhibits the TNF-huTNFR1 interaction or LTα-huTNFR1 interaction in vivo, as determined in an ex vivo cell-based assay. A further assay may be employed to exclude substantial side effects associated with cross-linking the TNFR1 receptor that would agonise the TNF-TNFR1 interaction. A suitable assay is determining the activity of the antibody or variant on HeLa or HT1080 cells for the absence of stimulatory activity to produce the inflammatory cytokines IL-6 or IL-8, respectively. An exemplary test is described in the examples section below.

Inhibition typically leads to a reduction of effects of huTNFR1 interaction or activity by at least 50%, or at least 60%, or at least 70%, or at least 80%, or at least 90%, or the maximum level. Methods for producing and characterizing an antibody described herein are well-known in the art. In a preferred embodiment, antibody variants are produced and screened for predefined properties using one or more cell-based assays employing huTNFR1 expressing cells or in vivo assays. For such assays, the antibody is typically added exogenously such that cells can be bound, e.g. in the presence and absence of TNF to determine the antagonistic and agonistic activity. These assays are typically based on the function of the immunoglobulin; that is, the ability of the antibody to bind to huTNFR1 and mediate some biochemical event, for example the blocking of TNF binding to said cells, e.g. in a competitive binding assay, TNF/receptor binding inhibition, the reduction of cytokine expression in the presence or absence of TNF, specifically inflammatory interleukins, such as IL-6 or IL-8, apoptosis, and the like.

The antibody described herein preferably has a TNF-antagonistic activity only (in particular, without detectable agonistic activity), thus, reducing the inflammatory reaction caused by an increased TNF level in the circulation that could result in undesired inflammatory responses, apoptosis and necrosis, or organ failure. The preferred antibody has an antagonistic activity corresponding to an $IC_{50}$ of less than 100 nM, preferably less than 20 nM, more preferred less than 10 nM, most preferred in the single digit nanomolar range or less, as measured in a cell-based assay employing TNF or LTalpha at a half-maximal saturation concentration, preferably in the range of 0.01-0.1 nM TNF and LTalpha, respectively.

A potential TNF-mimetic agonistic activity can be measured in the same cell-based assay, however, without employing TNF. The antibody described herein preferably has no significant agonistic activity, if the incubation of HeLa or HT1080 cells in the absence of TNF results in no or only marginal induction of cytokine, e.g. elevated IL-6 or IL-8 levels of less than 0.5 ng/ml at concentrations of at least 5 nM or around 10 nM of the antibody. Preferably there is no or only marginal or negative cytokine production, which can be determined by the amount of less than 10 pg/$10^5$ cells. In a preferred example the cytokine expression and release is less than 2.5 pg/100.000 cells in 18 h. Preferably the agonistic activity is thus below the basal level, or less than 2% of the response of a comparable TNF concentration, preferably less than 1% of the equivalent or maximal TNF response.

"Percent (%) amino acid sequence identity" with respect to the antibody sequences described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "antigen" as used herein is interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. The huTNFR1 antigen is an antigen comprising receptor structures which is capable to specifically bind trimeric TNF or LTα as a mono- or multimeric cytokine receptor on the surface of most human cells.

The term "huTNFR1" as used herein shall refer to CD120a TNFR1 (p55/60, TNFRSF1A tumor necrosis factor receptor superfamily, member 1A [Homo sapiens (human)], Gene ID: 7132) receptor of TNF, expressed ubiquitously on most human cells. A specific exemplary sequence of huTNFR1 is provided as SEQ ID NO:32.

The term "epitope" as used herein shall in particular refer to a molecular structure which may completely make up a specific binding partner or be part of a specific binding partner to a binding site of an antibody. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping.

Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen.

Herein the term "epitope" shall particularly refer to the epitope comprised in the huTNFR1, which is an epitope incorporated in the membrane-distal CRD1 and subdomain A1 of CDR2 of huTNFR1.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

With reference to polypeptides or proteins, such as isolated antibodies described herein, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

The term "recombinant" as used herein shall mean "being prepared by or the result of genetic engineering". A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host.

The antibody further described herein may be a recombinant antibody. To this end, the term "recombinant antibody", as used herein, includes antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library or library of antigen-binding sequences of an antibody, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

The antibody described herein is preferably provided as a recombinant protein produced by a recombinant expression system employing a host cell, e.g. by expression in the periplasmic space of E. coli or by expression as a secreted protein in a eukaryotic expression system such as yeast or mammalian, e.g. by CHO, HEK or human production host cell lines.

Chinese hamster ovary (CHO) cells have been most commonly used for antibody production. In addition to providing suitable glycosylation patterns, these cells allow consistent generation of genetically stable, highly productive clonal cell lines. They can be cultured to high densities in simple bioreactors using serum free media, and permit the development of safe and reproducible bioprocesses.

Host cells are most preferred, when being established, adapted, and completely cultivated under serum free conditions, and optionally in media which are free of any protein/peptide of animal origin.

"Specific" binding, recognizing or targeting as used herein, means that the binder, e.g., antibody or antigen-binding site of an antibody, exhibits appreciable affinity for the target antigen or a respective epitope in a heterogeneous population of molecules. Thus, under designated conditions (e.g., immunoassay), a binder specifically binds to the target antigen and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10-fold different (understood as at least 1 log difference), preferably the difference is at least 100-fold (understood as at least 2 logs difference), and more preferred a least 1000-fold (understood as at least 3 logs difference) as compared to another target. Differential binding may be determined by an immunoassay, preferably immunoblotting, ELISA or other immunological methods. The specificity of an antibody molecule for a particular target can be determined by competition assays, e.g. as described in Harlow, et al., ANTIBODIES: A LABORATORY MANUAL, Cold Spring Harbor Laboratory Press, Cold Spring Harbor, N.Y., 1988). Selective binding can be engineered or improved by recombinant antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

Use of the term "having the same specificity", "having the same binding site" or "binding the same epitope" indicates that equivalent monoclonal antibodies exhibit the same or essentially the same, i.e. similar immunoreaction (binding) characteristics and compete for binding to a pre-selected target binding sequence. The relative specificity of an antibody molecule for a particular target can be relatively determined by competition assays, e.g. as described in Harlow, et al., ANTIBODIES: A LABORATORY MANUAL, Cold Spring Harbor Laboratory Press, Cold Spring Harbor, N.Y., 1988).

Competition herein means a greater relative inhibition than about 30% as determined by competition ELISA analysis or by ForteBio analysis. It may be desirable to set a higher threshold of relative inhibition as criteria of what is a suitable level of competition in a particular context, e.g., where the competition analysis is used to select or screen for new antibodies designed with the intended function of the binding of the antigen. Thus, for example, it is possible to set criteria for the competitive binding, wherein at least 40% relative inhibition is detected, or at least 50%, at least 60%, at least 70%, at least 80%, at least 90% or even at least 100%, before an antibody is considered sufficiently competitive.

The term "patient" as used herein shall refer to human and other mammalian subjects. In particular the medical use described herein or the respective method of treatment applies to a subject in need of prophylaxis or treatment of NASH or of a disease condition associated with NASH. The subject may be a patient at risk of or suffering from NASH, including early stage or late stage disease. The term "patient" specifically includes subjects that receive prophylactic and/or therapeutic treatment. The term "treatment" is thus meant to include both prophylactic and therapeutic treatment.

Specifically, the term "therapy" refers to therapeutic measures which are intended to encompass administration to cure the disease or reduce the symptoms of disease.

Specifically, the term "prophylaxis" refers to preventive measures which are intended to reduce the risk of disease occurrence, or recurrence of disease.

The term "therapeutically effective amount", used herein interchangeably with any of the terms "effective amount" or "sufficient amount" of a compound, e.g. an antibody described herein, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from an inhibition of the TNF-TNFR1 interaction.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

As further described herein, a method of treating a patient comprises the step of administering a therapeutically effective amount of the above-defined huTNFR1-antibody to a patient in need thereof. A therapeutically effective amount typically is in the range of 0.5-500 mg, preferably 1-400 mg, even more preferred up to 300 mg, up to 200 mg, up to 100 mg or up to 10 mg, though higher doses may be indicated e.g. for treating obese patients or acute disease conditions.

A preferred pharmaceutical composition described herein comprises a therapeutically effective amount of the huTNFR1 antibody and optionally one or more additional components selected from the group consisting of a pharmaceutically acceptable carrier, pharmaceutically acceptable salts, an auxiliary agent, a stabilizer, a diluent and a solvent, or any combination thereof.

In one embodiment, an antibody described herein is the only therapeutically active agent administered to a patient. Alternatively, the antibody described herein is administered in combination with one or more other therapeutic agents, including but not limited to TNF antagonists, anti-inflammatory agents, cytokines, growth factors, or other therapeutic agents. The TNFR1-antagonistic antibody may be administered concomitantly or consecutively with one or more other therapeutic regimens, preferably with anti-TNF therapeutics, such as anti-TNF antibodies. The antibody described herein is preferably administered to the patient as a first-line treatment, or as a second-line therapy where anti-TNF therapeutics were not efficient, either as acute or chronic treatment. The specifically preferred medical use is for treating chronic disease.

Moreover, a treatment or prevention regime of a subject with a therapeutically effective amount of the antibody described herein may consist of a single administration, or alternatively comprise a series of applications. For example, the antibody may be administered at least once a year, at least once a half-year or at least once a month. However, in another embodiment, the antibody may be administered to the subject from about one time per week to about a daily administration for a given treatment. The length of the treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

"Nonalcoholic steatohepatitis (NASH)" is a liver disease, not associated with alcohol consumption, characterized by fatty change of hepatocytes, accompanied by intralobular inflammation and fibrosis. NASH is a common, often "silent" liver disease. It resembles alcoholic liver disease, but occurs in people who drink little or no alcohol. Three major features characterize NASH and distinguish it from other liver disease of metabolic origin: abnormal fat accumulation or deposition in the liver (liver steatosis), liver inflammation, and liver injury or hepatic tissue damage (fibrosis).

NASH is a potentially serious condition that carries a substantial risk of progression to end-stage liver disease, cirrhosis and hepatocellular carcinoma. Some patients who develop cirrhosis are at risk of liver failure and may eventually require a liver transplant. NAFLD may be differentiated from NASH by the NAFLD Activity Score (NAS), the sum of the histopathology scores of a liver biopsy for steatosis (0 to 3), lobular inflammation (0 to 2), and hepatocellular ballooning (0 to 2). A NAS of <3 corresponds to NAFLD, 3-4 corresponds to borderline NASH, and >5 corresponds to NASH. The biopsy is also scored for fibrosis (0 to 4).

As used herein, a patient suffering from NASH is a patient with NASH, or who has been diagnosed with NASH, or who is genetically predisposed to the development of NASH, or who may be predisposed to the development of NASH because he or she suffers from metabolic syndrome, obesity, diabetes or pre-diabetes. In still other embodiments a patient suffering from NASH is a patient that has been tested and found to display the clinical findings characteristic of NASH (abnormal accumulation of fat in the liver, liver inflammation and liver fibrosis), even though he or she may not show any physical symptoms of NASH yet. In some instances, a patient suffering from NASH displays symptoms of NASH even though a diagnosis has not been made yet.

Treatment of NASH may result in slowing down or halting the progression of NASH into cirrhosis. Some treatment regimen aim to delaying the onset of a physical symptom or set of physical symptoms or clinical manifestations or findings associated with NASH. In some embodiments, treatment results in the amelioration of at least one measurable physical symptom of NASH, such as, for example, weight loss, weakness or fatigue. In other embodiments, treatment results in amelioration of at least one clinical parameter or finding of NASH, such as, for example, abnormal liver fat accumulation, liver fibrosis as determined by biopsy, liver inflammation, abnormal levels of liver enzymes (e.g., ALT), abnormal levels of inflammatory cytokines or NAS score. In other embodiments, treatment results in the reduction, inhibition or slowing down of the progression of NASH, either physically by, e.g., stabilization of a measurable symptom or set of symptoms (such as fatigue, weight loss or weakness), or clinically/physiologically by, e.g., stabilization of a measurable parameter, such as abnormal fat accumulation in liver, abnormal levels of liver enzymes, abnormal levels of liver inflammatory markers, abnormal findings in a liver biopsy, NAS score or both. In another embodiment, treatment may also result in averting the cause and/or effects or clinical manifestation of NASH, or one of the symptoms developed as a result of NASH, prior to the disease or disorder fully manifesting itself. In some embodiments, treatment results in an increase in survival rate or survival time in a patient with NASH. In some embodiments, treatment results in the reduction of the potential for a patient with NASH needing a liver transplant. In other embodiments, treatment results in the elimination of the need for a NASH patient to undergo a liver transplant. In other embodiments, it results in the reduction of chances a patient with NASH will develop cirrhosis. In other embodiments, it results in prevention of progression to cirrhosis as determined by histology.

Specific embodiments described herein refer to "monoclonal" antibodies (mAbs). Monoclonal antibodies are produced by cloning the antibody genes into monoclonal host cell or respective cell lines. Monoclonal antibodies can be produced using any method that produces antibody molecules by cell lines in culture, e.g. cultivating recombinant eukaryotic (mammalian or insect) or prokaryotic (bacterial) host cells. Examples of suitable methods for preparing monoclonal antibodies include the hybridoma methods of Kohler & Milstein (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

Antibodies described herein may be identified or obtained employing a hybridoma method. In such method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Monoclonal antibodies may then be purified from hybridoma supernatants for further testing for its specific binding of the target antigen, and engineering of antibodies, e.g. for different diagnostic or therapeutic purposes.

huTNFR1-specific antibodies, in some instances, emerge through screening against the huTNFR1 antigen. To increase the likelihood of isolating differentially binding clones one would apply multiple selective pressures by processively screening against different antigens or epitopes.

Screening methods for identifying antibodies with the desired selective binding properties may be done by display technologies using a library displaying antibody sequences or antigen-binding sequences thereof (e.g. using phage, bacterial, yeast or mammalian cells; or in vitro display systems translating nucleic acid information into respective (poly)peptides). Reactivity can be assessed based on ELISA, Western blotting or surface staining with flow cytometry, e.g. using standard assays.

Isolated antigen(s) may e.g. be used for selecting antibodies from an antibody library, e.g. a phage-, phagemid- or yeast-displayed antibody library.

Specific embodiments described herein refer to "pharmaceutical compositions", such compositions may comprise the antibody as described herein and a pharmaceutically acceptable carrier and/or excipient, in particular to obtain an artificial, non-naturally occurring composition. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination described herein. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an antibody may be dissolved in saline, water, polyethylene glycol, propylene glycol, carboxymethyl cellulose colloidal solutions, ethanol, corn oil, peanut oil, cotton-seed oil, sesame oil, tragacanth gum, and/or various buffers. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein the antibody described herein and one or more therapeutically active agents are formulated. Stable formulations of the antibody described herein are prepared for storage by mixing said antibody having the desired degree of purity with optional pharmaceutically acceptable carriers, excipients or stabilisers, in the form of lyophilized formulations or aqueous solutions. The formulations to be used for in vivo administration are sterile. This is readily accomplished by filtration through sterile filtration membranes or other methods. The antibody and other therapeutically active agents disclosed herein may also be formulated as immunoliposomes, and/or entrapped in microcapsules.

Administration of the pharmaceutical composition comprising an antibody described herein, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, e.g. employing inhalable technology or pulmonary delivery systems, vaginally, parenterally, rectally, or intraocularly.

Examplary formulations as used for parenteral administration include those suitable for subcutaneous, intramuscular or intravenous injection as, for example, a sterile solution, emulsion or suspension.

In one embodiment, the antibody described herein is the only therapeutically active agent administered to a subject, e.g. as a disease modifying or preventing monotherapy.

In another embodiment, the antibody described herein is combined with further active substances, e.g. in a mixture or kit of parts, to treat a subject in need of therapy or prophylaxis, such as a disease modifying or preventing combination therapy.

The combination with one or more other therapeutic or prophylactic agents may include standard treatment, e.g. antibiotics, steroid and non-steroid inhibitors of inflammation, and/or other antibody based therapy. The combination may specifically comprise agents which are used for treating the primary disease, where inflammatory processes would lead to secondary inflammatory, degenerative or malignant disease conditions. The primary disease is e.g. NASH and the combination would e.g. include NSAID or other novel drugs such as FXR-agonists, GLP1R-agonists, or PPAR-agonists.

In a combination therapy, the antibody may be administered as a mixture, or concomitantly with one or more other therapeutic regimens, e.g. either before, simultaneously or after concomitant therapy.

The biological properties of the antibody or the respective pharmaceutical preparation described herein may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic or as a prophylactic with the appropriate half-life, effector function, inhibitor activity and/or immune response upon passive immunotherapy. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the antibody and respective pharmaceutical compositions described herein may be tested in humans to determine their therapeutic or prophylactic efficacy, toxicity, immunogenicity, pharmacokinetics, and/or other clinical properties.

Therefore, the invention provides for a new method of treatment of NASH, and in particular those disease conditions that are associated to NASH. It was surprising that an anti-TNFR1 antibody was significantly improving liver steatosis and histological disease activity in NASH, as shown in a mouse model. TNFR1-inhibition resulted in a significant reduction of the percentage of liver steatosis as well as triglyceride content. In addition, the NAFLD activity score which considers steatosis, ballooing and lobular inflammation was significantly decreased by the anti-TNFR1 antibody treatment. It was unexpected that selective TNFR1-inhibition was improving liver fibrosis in an NAFLD mouse model, and was even able to treat and liver fibrosis by reducing fibrosis in liver tissue. It was further shown that anti-TNFR1 antibody treatment was able to reduce apoptosis in liver tissues. Further, a significant reduction of ALT and insulin serum levels was achieved. Thus, treatment with an anti-TNFR1 antibody resulted in a significant improvement of inflammation and insulin resistance in NAFLD.

It was particularly surprising that an anti-TNFR1 antibody significantly improves liver steatosis and histological disease activity in NASH in view of the prior art, because development of NASH or steatosis had been reported as side effect of TNFi therapy. Feagins et al. reported that patients with Crohn's disease, rheumatoid arthritis, psoriatic arthritis and ankylosing spondylitis who were treated with either infliximab, adalimumab or etanercept developed abnormal ALT levels during TNFi treatment and showed NAFLD (NASH or steatosis) in liver biopsies (Eur J Gastroenterol Hepatol. 2015, 27(10):1154-1160). It was thus highly unexpected that, selective inhibition of TNFR1 is effective against NASH.

Exemplary antibodies described herein are e.g., full-length antibodies produced according to WO2012035141, and/or its parental mouse antibody H398 as described in WO2008113515A2, affinity-matured functionally active variants and/or antibody fragments of any of the foregoing, or those antibodies which are monovalent anti-huTNFR1 binders and comprise the antigen-binding site of any of the foregoing, such as the monovalent antibodies described in WO2017174586 A1.

The present invention is further illustrated by the following examples without being limited thereto.

EXAMPLES

Example 1

Improvement of Liver Steatosis and Histological Disease Activity in Mice with Experimental NAFLD Methods:
B6-huTNFR1-k/i-mice received a high fat diet (HFD) consisting of 60% kcal fat+fructose/saccharose in the drinking water (Kohli R et al., Hepatology 2010) for 24 weeks complemented with either anti-TNFR1 (Atrosab) or control antibody (Cetuximab, an anti-EGFR antibody, Erbitux®, ImClone Systems, Bristol-Myers Squibb and Merck KGaA) treatment (20 mg/kg bodyweight, 2x/w) for further 8 weeks.

The Atrosab antibody used herein is a full-length antibody produced according to WO2012035141 and comprising the antigen-binding site incorporated in the combination of a VH and a VL domain, comprising six CDR sequences, which are:
SEQ ID NO:23: VH-CDR1
SEQ ID NO:24: VH-CDR2
SEQ ID NO:25: VH-CDR3
SEQ ID NO:26: VL-CDR1
SEQ ID NO:27: VL-CDR2
SEQ ID NO:28: VL-CDR3.

At the end of treatment, liver tissues from the differentially treated mice were compared for liver steatosis, NAFLD activity score, apoptosis and fibrosis.

The percentage of steatosis as well as the NAFLD activity score (NAS) according to Kleiner et al. (Hepatology 2005) was assessed by a pathologist. Triglyceride content was determined in homogenized liver tissues by using an enzyme test (Roche Diagnostics). Apoptosis was investigated by immunohistochemistry using an antibody for activated caspase-3 (Cell Signaling). Fibrosis was detected by Sirius Red staining according to the protocol of the manufacturer (Sigma Aldrich) and quantified as described (Schindelin J et al., Nat Methods 2012).

Sera were analyzed for ALT levels by a kinetic UV test (Beckman Coulter) and insulin levels were measured using the ultra-sensitive mouse insulin ELISA Kit (Crystal Chem.) according to manufacturer's instructions.

Results:
Atrosab-treatment resulted in a significant improvement of liver steatosis and histological disease activity in mice with experimental NAFLD.

Liver tissues of HFD-mice treated with anti-TNFR1 antibody (Atrosab) or control (Cetuximab) antibody were histologically analyzed for the percentage of liver steatosis, triglyceride content and disease activity assessed by NAFLD activity score (NAS). Compared to mice treated with the control antibody, TNFR1-inhibition resulted in a significant reduction of the percentage of liver steatosis ($p<0.05$; FIG. 1A) as well as triglyceride content ($p<0.01$; FIG. 1B). In addition, the NAFLD activity score (NAS) which considers steatosis, ballooning and lobular inflammation, significantly ($p<0.05$) decreased in Atrosab-treated compared to control mice (FIG. 1C).

Example 2

Selective TNFR1-Inhibition is Associated with Improvement of Liver Fibrosis in the NAFLD Mouse Model Having demonstrated that selective TNFR1-inhibition improves liver steatosis and NAS, the effect of Atrosab on fibrosis reduction was analyzed. Improvement of liver fibrosis was demonstrated, assessed by Sirius Red staining, in mice treated with the anti-TNFR1-antibody compared to those treated with control antibody (FIG. 2A). Quantification of the fibrotic area revealed a significant ($p<0.05$) fibrosis reduction in liver tissues from mice treated with anti-TNFR1-antibody compared to control mice (FIG. 2B).

Example 3

Reduced Apoptosis in Liver Tissues of NAFLD Mice Treated with Anti-TNFR1 Antibody In initial experiments mice received HFD for 20 weeks including a 4 week treatment with either anti-TNFR1 or control antibody. It was demonstrated that anti-TNFR1 antibody treatment is able to reduce apoptosis, assessed by immunohistochemical analysis of active caspase-3, already within a 4 week treatment period. Compared to control antibody, a significant ($p<0.05$) reduction of active caspase-3 could be observed in liver tissues of mice treated with the anti-TNFR1 antibody (FIG. 3).

Example 4

Improvement of ALT and Insulin Levels in Sera of NAFLD Mice Treated with Anti-TNFR1 Antibody In line with the observation of improved histology of mice treated with anti-TNFR1 antibody (FIGS. 1 and 2), a significant ($p<0.05$) reduction of ALT (FIG. 4A) and insulin (FIG. 4B) serum levels in mice treated with anti-TNFR1 antibody compared to those treated with control antibody was demonstrated. Thus, selective anti-TNFR1 inhibition resulted in a significant improvement of inflammation and insulin resistance.

Example 5

Description of Atrosimab—Production and Characterization

Materials

The Atrosab antibody was obtained as described in Example 1. Recombinant human TNFR1-Fc fusion protein was produced as described in WO2012035141. Atrosimab (HC: SEQ ID NO:18; LC:SEQ ID NO:13) was produced and purified after lentiviral transduction in CHO cells by Catalent (Catalent Pharma Solutions, Somerset, Ewing, N.J., US). Anti-His-HRP (HIS-6 His-Probe-HRP, sc-8036) was purchased from Santa Cruz Biotechnology (Santa Cruz, Calif., USA). Anti-human IgG A (Goat, polyclonal, 2010-01) was acquired from SouthernBiotech and anti-human IgG B (Goat, polyclonal, MBS571163) as well as anti-human IgG B (Goat, polyclonal, MBS571678) from MyBioSource, (San Diego, Calif., USA). Furthermore, anti-human IgG (Fab specific, A 0293) and anti-human IgG (Fc specific, A 0170) was purchased from Sigma-Aldrich (Taufkirchen, Germany).

Protein Production

The reference protein Fab 13.7 was produced as described in WO2017174586A1 in transiently transfected HEK 293E cells using polyethylenimine (linear, 25 kDa, Sigma-Aldrich, Taufkirchen, Germany) and purified by protein affinity chromatography strictly as recommended by the manufacturer (CaptureSelect™ IgG-CH1 Affinity Matrix, 194320005, Thermo Fisher Scientific, Dreieich, Germany).

Protein Characterization

Purity and correct assembly of Atrosimab was analyzed by SDS-PAGE using 4 µg of purified protein in presence and absence of beta-mercaptoethanol as reducing agent. Proteins in the gel were stained using Coomassie-Brilliant Blue and gels were de-stained with water. Intact protein was analyzed by size-exclusion chromatography using a Waters 2695 HPLC and a Phenomenex Yarra SEC-2000 column (300×7.8 mm). Standard proteins: Thyroglobulin (669 kDa), Apoferritin (443 kDa), Alcohol dehydrogenase (150 kDa), BSA (66 kDa), Carbonic anhydrase (29 kDa), FLAG peptide (1 kDa).

Thermal Stability

The melting/aggregation Temperature ($T_m$) of Atrosimab was determined by dynamic light scattering (ZetaSizer Nano Z S, Malvern, Herrenberg, Germany) using 100 µg of purified protein in PBS. The applied temperature was increased in 1° C. intervals from 35° C. to 80° C. with equilibration times of 2 minutes prior to each measurement. The $T_m$ was determined by visual interpretation of the increasing signal (kcps).

Plasma Stability

Samples of purified Atrosimab were diluted in human plasma to a concentration of 100 nM and incubated at 37° C. for 1, 3 and 7 days. Subsequent analysis of the remaining binding capacity to human TNFR1 was performed by ELISA after serial dilution in 2% skim milk in PBS (2% MPBS) by steps of 1 to 3.16 (square root of 10). Control samples were incubated at 4° C. in PBS for 7 days or directly frozen after dilution in human plasma.

Enzyme-Linked Immunosorbent Assay (ELISA)

Microtiter plates were coated with 100 µl of TNFR1-Fc fusion protein (1 µg/ml in PBS) and incubated at 4° C. overnight. The residual binding sites were blocked with 2% MPBS (skim milk in PBS, 200 µl per well) at room temperature for 2 hours and subsequently washed twice with PBS. 100 µl of the samples diluted in 2% MPBS were incubated at room temperature for 1 hour prior to the last incubation step with 100 µl of the HRP conjugated detection antibodies in 2% MPBS. Bound protein was detected with 100 µl TMB substrate solution (1 mg/ml 3,3',5,5'-Tetramethylbenzidine[TMB], 0.006% $H_2O_2$ in 100 mM Na-acetate buffer, pH 6 at RT), the HRP-reaction was stopped by the addition of 50 µl 1M $H_2SO_4$ and the absorption at the wavelength of 450 nm was measured using the Infinite microtiter plate reader (TECAN, Maennedorf, Switzerland). Between each incubation step and in advance of the detection, the plates were washed twice times with PBST and twice with PBS.

Affinity Measurements Using the Quartz Christal Microbalance

Real-time binding dynamics in protein-protein interactions were determined by quartz crystal microbalance measurements (Cell-200 C-Fast, Attana, Stockholm, Sweden). One of the binding partners (TNFR1-Fc) was chemically immobilized on a LNB Carboxyl Sensor Chip (3623-3103, Attana, Stockholm, Sweden) according to the manufacturer's protocol at a moderate density of ~94 ΔHz. Binding experiments were performed with samples (analyte) diluted in PBST (PBS, 0.1% Tween 20) between 128 nM and 4 nM (1:2 dilution steps) at pH 7.4 with a flow rate of 25 µl/min at 37° C. The chip was regenerated with 25 µl 20 mM glycine, pH 2.0. Every third measurement, an injection of running buffer was measured which was subtracted from the binding curve prior to data analysis. Data were collected using the software provided by Attana and analyzed by Attaché Office Evaluation software (Attana, Stockholm, Sweden) and TraceDrawe (ridgview instruments, Vange, Sweden).

Interleukin Release Assay $2 \times 10^4$ HeLa or HT1080 cells per well were seeded into a 96 well microtiter plate and grown in 100 µl RPMI 1640+5% FCS overnight. The next day, the supernatants were exchanged in order to remove constitutively produced cytokines. The cells were incubated with dilution series of samples in RPMI 1640+5% FCS at 37° C., 5% $CO_2$. In the case of competition experiments, both analyzed protein samples were prepared individually (either titrated or diluted to a single concentration) and added to the plate subsequently. Non-stimulated cells served as control. After 16-20 hours, the plates were centrifuged at 500 g for 5 minutes and cell supernatants were analyzed directly by ELISA, which was performed according to the protocol of the manufacturer. Supernatants were diluted in RPMI 1640 (without FCS) and antibodies were diluted in Reagent Diluent (0.1% BSA, 0.05% A Tween 20, 20 mM TRIS, 150 mM NaCl, pH7.5). The coated microtiter plates were blocked using 1% BSA (Bovine Serum Albumin) in PBS and washing as well as detection and measuring were performed as described above for ELISA. Sandwich ELISA kits for the detection of IL-6 and IL-8 in the cell culture supernatant were purchased from ImmunoTools, (Friesoythe, Germany).

Cytotoxicity/Cell Viability Assay

Cells ($1 \times 10^4$ per well) were seeded into 96-well microtiter plates and incubated over night at 37° C. and 5% $CO_2$. The proteins were diluted in RPMI 1640+10% FCS and added to the cells. Cytotoxicity assays were incubated at 37° C., 5% $CO_2$ for 24 hours before the supernatant was discarded and 50 µl crystal violet solution was added to the wells. Subsequently, the plates were washed in dd$H_2O$ for 20 times and dried. The remaining violet dye, resulting from living and adherent cells, which were fixed by the methanol contained in the staining solution, was dissolved by the addition of 100 µl methanol upon shaking at RT for 10 minutes. Plates were measured using the Infinite microtiterplate reader (Tecan, Maennedorf, Switzerland).

Pharmacokinetics

Transgenic C57BL/6J mice, bearing the gene of the extracellular domain of human TNFR-1 at the locus of the particular mouse gene (C57BL/6J-huTNFRSF1Aecdtm1UEG/izi, Dong et al., 2016), received an intravenous injection of 400 µg Atrosimab. Blood samples were collected after 3 min, 30 min, 1 h, 2 h and 6 h as well as after 3 days and 7 days and incubated on ice immediately. Serum was separated by centrifugation (13.000 g, 4° C., 10 minutes) and stored at −20° C. Remaining protein in the serum was detected by binding ELISA as described above. The ELISA signal was interpolated from a freshly prepared standard binding curve of the analyzed protein. Determined concentrations were plotted against time and pharmacokinetic constants were obtained upon analysis using PKsolver add-in for Microsoft Excel.

Example 5.1

Biochemical Characterization of Atrosimab

A monovalent Tumor necrosis factor (TNF) receptor 1 (TNFR1)-specific antagonist, designated Atrosimab, was generated by fusing the variable domains of Fab 13.7 to the N-termini of a heterodimerizing Fc module Fc1k (one/ kappa). This process resulted in a Fab-like monovalent molecule of increased size, equipped with the ability to interact with the neonatal Fc receptor in order to enable extended serum circulation (FIG. 6a). The resulting drug candidate Atrosimab was produced in CHO cells after several rounds of lentiviral transduction, purified by protein A affinity chromatography and consecutive size exclusion chromatography (SEC) by Catalent Pharma Solutions (Catalent Pharma Solutions, Somerset, Ewing, N.J., US).

Atrosimab revealed a single peak in SEC at a retention time of 17.9 minutes with an interpolated molecular weight of 81 kDa and a stokes radius $r_S$ of 3.5 nm (FIG. 6b). In SDS-PAGE under reducing conditions, two bands of 38 kDa and 43 kDa were detected as well as one band of 70 kDa under non-reducing conditions (FIG. 6c). These data correspond well to the calculated molecular mass of 72 kDa (composed of 35 kDa and 36 kDa chains), indicate proper expression of both polypeptide chains and correct assembly of the functional heterodimeric protein. Furthermore, Atrosimab revealed an aggregation point ($T_m$) of 64° C. as determined by dynamic light scattering (DLS, FIG. 6d), which is comparable to that of intact IgG molecules analyzed also by DLS (Martin et al., 2014, Brader et al., 2015)). Finally, binding activity of Atrosimab to human TNFR1-Fc remained unaltered after incubation in human plasma for up to 7 days, indicating good plasma stability (FIG. 6e).

Example 5.2

Binding of Atrosimab to TNFR1, Fcγ Receptors and the Complement Protein C1q

The interaction of Atrosimab with its target receptor TNFR1 was analyzed by ELISA under equilibrium conditions, resulting in an $EC_{50}$ value of 0.4 nM (FIG. 7a), representing a two-fold reduction in binding activity, when compared to the parental Fab 13.7 and a four-fold reduction in comparison to the bivalent IgG ATROSAB. Moreover, Atrosimab bound in a real-time binding study using a quartz crystal microbalance to human TNFR1, immobilized at a moderate receptor density of ~94 ΔHz, with an apparent $K_D$ value of 2.7 nM, and $k_{on}$ $3.7 \times 10^5 M^{-1} s^{-1}$ of and an $k_{off}$ of $9.8 \times 10^{-4}$ $s^{-1}$ (FIG. 7b), as analyzed by a 1:1 binding algorithm. Of note, Atrosimab comprises an Fc region which is modified to reduce antibody-mediated effector functions (Armour et al., 1999). Accordingly, Atrosimab revealed an almost complete lack of binding to human Fcγ receptors Ia, IIb and IIIa as well as to the complement protein C1q as demonstrated by ELISA (FIG. 7c). Binding was reduced to a similar extent (FcγRI and FcγRIII) or even more pronounced (FcγRIIb and C1q) when compared to the previously described anti-human TNFR1 IgG ATROSAB (Zettlitz et al., 2010), which carries the identical Fc modifications with respect to Fcγ receptor and C1q binding.

Example 5.3

Atrosimab Inhibits TNFR1 Activation In Vitro and Lacks any Agonistic Activity

Atrosimab revealed complete absence of any agonistic bioactivity within an analyzed concentration range between 50 pM and 500 nM in interleukin (IL) release experiments, using HeLa cells to analyze IL-6 and HT1080 cells for IL-8, as well as in cell death induction assays using Kym-1 cells (FIG. 3a-c). An identical lack of agonism was detected in case of the parental Fab 13.7. In contrast, the bivalent IgG ATROSAB induced a marginal release of IL-6 and IL-8 at concentrations between 1 nM and 100 nM (FIGS. 8a and b), which confirmed previously published data (Richter et al., 2013). In contrast, the marginal agonistic activity of ATROSAB could not be detected in the Kym-1 cell death induction assay (FIG. 8c).

Furthermore, Atrosimab inhibited the activation of TNFR1, induced by 0.1 nM TNF in the HeLa IL-6 release assay and in the HT1080 IL-8 release assay with $EC_{50}$ values of 54.5 nM and 24.2 nM, respectively (FIGS. 8d and e). Moreover, cell death, induced by 0.1 nM TNF in Kym-1 cells, was inhibited by Atrosimab with an $IC_{50}$ value of 16.2 nM (FIG. 8f). When compared to the parental Fab 13.7, these data represent a 1.5-fold to 1.9-fold reduction in bioactivity (Table 1). However, compared to the bioactivity of the bivalent IgG ATROSAB, Atrosimab demonstrated 3.0-fold, 3.5-fold and 4.0-fold more potent inhibition of TNF-mediated TNFR1 activation, as determined in the IL-6 release assay, the IL-8 release assay and the cell death induction assay, respectively (Table 1).

TABLE 1

| Bioactivity of Atrosimab | | | |
|---|---|---|---|
| | Atrosimab | Fab 13.7 | ATROSAB |
| $IC_{50}$, IL-6 [nM] | 54.5 | 37.1 | 164.7 |
| $IC_{50}$, IL-8 [nM] | 24.2 | 12.7 | 84.1 |
| $IC_{50}$, Cell death induction [nM] | 16.2 | 9.5 | 64.4 |

Addressing the potential risk of secondary crosslinking of Atrosimab, mediated by e.g. anti-drug antibodies (ADAs), the agonistic potential of Atrosimab was analyzed in the presence of three different mouse anti-human IgG sera in IL-8 release assays using HT1080 cells (Richter et a. 2013). Binding of mouse anti-human IgG sera to Atrosimab, Fab 13.7 and ATROSAB was demonstrated by ELISA (data not shown). Notably, Atrosimab did not induce any release of IL-8 within the analyzed concentration range (50 pM to 500 nM), which was also observed for the parental Fab 13.7 (FIG. 9a-c). In contrast, the bivalent IgG ATROSAB induced clearly increased release of IL-8 (FIG. 9a-c), when compared to the marginal release observed in FIG. 8, indicating a clearly reduced propensity of Atrosimab to mediate any activation of TNFR1 even in the presence of drug-specific antibodies, when compared to ATROSAB.

Example 5.4

Pharmacokinetics of Atrosimab

Finally, pharmacokinetic properties of Atrosimab were recorded after bolus injection of 400 μg protein using C57BL/6J-huTNFRSF1A$_{ecd}^{tm1UEG}$/izi (Dong et al., 2016) mice which carry a transgene of the extracellular domain of human TNFR1 (FIG. 10, Table 2). Atrosimab was eliminated from the mouse circulation with an initial half-live of 2.2±1.2 hours and a terminal half-live of 41.8±18.1 hours, resulting in an area under the curve of 5856.0±1369.9 μg/ml×h.

TABLE 2

Pharmakokinetic Analysis of Atrosimab

| | |
|---|---|
| $t_{1/2}\alpha$ (h) | 2.2 ± 1.2 |
| $t_{1/2}\beta$ (h) | 41.8 ± 18.1 |
| $C_0$ (μg/ml) | 324.7 ± 53.5 |
| AUC 0-t (μg/ml × h) | 5856.0 ± 1369.9 |
| $V_{ss}$ (μg/(μg/ml)) | 3.4 ± 1.3 |
| CL ((μg)/(μg/ml)/h) | 0.29 ± 0.20 |

$t_{1/2}\alpha$, initial half-life;
$t_{1/2}\beta$, terminal half-life;
$C_0$, interpolated initial concentration;
AUC 0-t, area under the curve until the lase detected time point;
$V_{ss}$, volume of distribution (at steady state);
CL, clearance.

REFERENCES

Armour K L, Clark M R, Hadley A G, Williamson L M. Recombinant human IgG molecules lacking Fcgamma receptor I binding and monocyte triggering activities. Eur J Immunol. 1999 August;29(8):2613-24.

Brader M L, Estey T, Bai S, Alston R W, Lucas K K, Lantz S, Landsman P, Maloney K M. Examination of thermal unfolding and aggregation profiles of a series of developable therapeutic monoclonal antibodies. Mol Pharm. 2015 Apr. 6;12(4):1005-17. doi: 10.1021/mp400666b.

Dong Y, Fischer R, Naudé P J, Maier O, Nyakas C, Duffey M, Van der Zee E A, Dekens D, Douwenga W, Herrmann A, Guenzi E, Kontermann R E, Pfizenmaier K, Eisel U L. Essential protective role of tumor necrosis factor receptor 2 in neurodegeneration. Proc Natl Acad Sci USA 2016; 113: 12304-9; PMID:27791020; https://doi.org:10.1073/pnas.1605195113

Martin N, Ma D, Herbet A, Boquet D, Winnik F M, Tribet C. Prevention of thermally induced aggregation of IgG antibodies by noncovalent interaction with poly(acrylate) derivatives. Biomacromolecules. 2014 Aug. 11;15(8):2952-62. doi: 10.1021/bm5005756.

Zettlitz K A, Lorenz V, Landauer K, Winkel S, Herrmann A, Scheurich P, Pfizenmaier K, Kontermann R. ATROSAB, a humanized antagonistic anti-tumor necrosis factor receptor one-specific antibody. MAbs. 2010 November-December;2 (6):639-47. Epub 2010 Nov. 1.

The invention claimed is:

1. A method of treating nonalcoholic steatohepatitis (NASH) and disease conditions associated thereto in a subject in need thereof, comprising administering to the subject an effective amount of an antagonist antibody specifically recognizing human tumor necrosis factor receptor 1 (huTNFR1).

2. The method of claim 1, wherein the antibody is a monoclonal antibody.

3. The method of claim 1, wherein the antibody is a monospecific, bivalent, full-length antibody.

4. The method of claim 3, wherein the antibody comprises an IgG1 Fc domain which is deficient in mediating effector function.

5. The method of claim 1, wherein the antibody monovalently recognizes the huTNFR1.

6. The method of claim 1, wherein the antibody comprises
a) a heavy chain variable domain (VH) comprising the complementarity-determining regions (CDRs): VH-CDR1, VH-CDR2, and VH-CDR3; and
b) a light chain variable domain (VL) comprising the CDRs: VL-CDR1, VL-CDR2, and VL-CDR3,
wherein
i)
VH-CDR1 comprises or consists of SEQ ID NO:1;
VH-CDR2 comprises or consists of SEQ ID NO:2
VH-CDR3 comprises or consists of SEQ ID NO:3
VL-CDR1 comprises or consists of SEQ ID NO:4
VL-CDR2 comprises or consists of SEQ ID NO:5
VL-CDR3 comprises or consists of SEQ ID NO:6;
or
ii)
VH-CDR1 comprises or consists of SEQ ID NO:23;
VH-CDR2 comprises or consists of SEQ ID NO:24
VH-CDR3 comprises or consists of SEQ ID NO:25
VL-CDR1 comprises or consists of SEQ ID NO:26
VL-CDR2 comprises or consists of SEQ ID NO:27
VL-CDR3 comprises or consists of SEQ ID NO:28;
wherein numbering is according to the Kabat EU index;
or a functionally active variant of any of i) or ii) above, which comprises up to 1 or 2 point mutations point mutations in each of the CDR sequences, and which specifically recognizes the huTNFR1.

7. The method of claim 1, wherein the antibody comprises a VH sequence comprising or consisting of SEQ ID NO:7 or 9; and a VL sequence comprising or consisting of SEQ ID NO:8 or 10, or a functionally active variant thereof comprising up to 1 point mutation in each of the CDR sequences, and at least 60% sequence identity in the framework (FR) sequences FR1-4 of VH and VL.

8. The method of claim 1, wherein the disease conditions are any of hepatic steatosis, inflamed liver, liver fibrosis and hepatocellular carcinoma.

9. The method of claim 1, wherein an effective amount of the antibody is administered to the subject to antagonize TNFa/huTNFR1 signaling.

10. The method of claim 1, wherein an effective amount of the antibody is administered to the subject to reduce any one or more of
a) steatosis, triglyceride content, inflammation, and/or apoptosis in liver tissue;
b) the serum aminotransferase level;
c) insulin-resistance and optionally to improve glucose-tolerance; and/or
d) the NAFLD activity score.

11. The method of claim 1, wherein the antibody is administered to the subject at a dose ranging from 0.05 mg/kg to 20 mg/kg.

12. The method of claim 1, wherein the antibody is administered to the subject in combination with a treatment with anti-inflammatory drugs, or therapies using a farnesoid X receptor (FXR) agonist, a glucagon-like peptide-1 receptor (GLP1R) agonist, or a peroxisome proliferator-activated receptor (PPAR) agonist.

13. The method of claim 1, wherein the subject is also suffering from type II diabetes mellitus, type I diabetes mellitus, pre-diabetes, insulin resistance, or obesity, wherein obesity is defined as the patient having a body mass index of at least 30.

14. The method of claim 1, wherein the antibody recognizes an epitope represented by amino acids 1 to 115 in the N-terminal region of huTNFR1.

15. The method of claim 4, wherein the antibody comprises at least one mutation selected from the group consisting of E233P, L234V, L235A, ΔG236, A327G, A330S and P331S, wherein numbering is according to the Kabat EU index.

16. The method of claim 15, wherein the antibody comprises A327G/A330S/P331S.

* * * * *

UNITED STATES PATENT AND TRADEMARK OFFICE
CERTIFICATE OF CORRECTION

PATENT NO. : 11,028,178 B2
APPLICATION NO. : 16/766841
DATED : June 8, 2021
INVENTOR(S) : Heike Bantel, Klaus Pfizenmaier and Andreas Herrmann It is certified that error appears in the above-identified patent and that said Letters Patent is hereby corrected as shown below:

On the Title Page

Item (73) The Assignee's name reads:
BALIOPHARMA AG

Should now read:
BALIOPHARM AG

Signed and Sealed this
Third Day of September, 2024

Katherine Kelly Vidal
*Director of the United States Patent and Trademark Office*

SEQUENCE LISTING

```
<160> NUMBER OF SEQ ID NOS: 33

<210> SEQ ID NO 1
<211> LENGTH: 5
<212> TYPE: PRT
<213> ORGANISM: Artificial Sequence
<220> FEATURE:
<223> OTHER INFORMATION: CDR

<400> SEQUENCE: 1

Asp Phe Tyr Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (3)..(3)
<223> OTHER INFORMATION: X at position 3 is any of Y or V
<220> FEATURE:
<221> NAME/KEY: MISC_FEATURE
<222> LOCATION: (5)..(5)
<223> OTHER INFORMATION: X at position 5 is any of Y, T, S or G
<220> FEATURE:
<221> NAME/KEY: MISC_FEATURE
<222> LOCATION: (6)..(6)
<223> OTHER INFORMATION: X at position 6 is any of S or Q
<220> FEATURE:
<221> NAME/KEY: MISC_FEATURE
<222> LOCATION: (8)..(8)
<223> OTHER INFORMATION: X at position 8 is any of H or E
```

```
<220> FEATURE:
<221> NAME/KEY: MISC_FEATURE
<222> LOCATION: (10)..(10)
<223> OTHER INFORMATION: X at position 10 is any of Y or K
<220> FEATURE:
<221> NAME/KEY: MISC_FEATURE
<222> LOCATION: (13)..(13)
<223> OTHER INFORMATION: X at position 13 is any of E or D

<400> SEQUENCE: 2

Glu Ile Xaa Pro Xaa Xaa Gly Xaa Ala Xaa Tyr Asn Xaa Lys Phe Lys
1               5                   10                  15

Ala

<210> SEQ ID NO 3
<211> LENGTH: 6
<212> TYPE: PRT
<213> ORGANISM: Artificial Sequence
<220> FEATURE:
<223> OTHER INFORMATION: CDR

<400> SEQUENCE: 3

Trp Asp Phe Leu Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: CDR

<400> SEQUENCE: 4

Arg Ser Ser Gln Ser Leu Leu His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR

<400> SEQUENCE: 5

Thr Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (3)..(3)
<223> OTHER INFORMATION: X at position 3 is any of S or G

<400> SEQUENCE: 6

Ser Gln Xaa Thr His Val Pro Tyr Thr
1               5

<210> SEQ ID NO 7
<211> LENGTH: 115
<212> TYPE: PRT
<213> ORGANISM: Artificial Sequence
<220> FEATURE:
<223> OTHER INFORMATION: VH
```

```
<400> SEQUENCE: 7

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: VL

<400> SEQUENCE: 8

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
            100                 105                 110

Arg Thr Val Ala Ala
        115

<210> SEQ ID NO 9
<211> LENGTH: 115
<212> TYPE: PRT
<213> ORGANISM: Artificial Sequence
<220> FEATURE:
<223> OTHER INFORMATION: VH

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45
```

```
Gly Glu Ile Tyr Pro Tyr Ser Gly His Ala Tyr Tyr Asn Glu Lys Phe
        50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
                100                 105                 110

Val Ser Ser
        115

<210> SEQ ID NO 10
<211> LENGTH: 113
<212> TYPE: PRT
<213> ORGANISM: Artificial Sequence
<220> FEATURE:
<223> OTHER INFORMATION: VL

<400> SEQUENCE: 10

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
                100                 105                 110

Arg

<210> SEQ ID NO 11
<211> LENGTH: 218
<212> TYPE: PRT
<213> ORGANISM: Artificial Sequence
<220> FEATURE:
<223> OTHER INFORMATION: Heavy chain

<400> SEQUENCE: 11

His Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
            35                  40                  45

Gly Glu Ile Val Pro Ser Gln Gly Glu Ala Lys Tyr Asn Asp Lys Phe
        50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
                100                 105                 110
```

```
Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
    210                 215

<210> SEQ ID NO 12
<211> LENGTH: 219
<212> TYPE: PRT
<213> ORGANISM: Artificial Sequence
<220> FEATURE:
<223> OTHER INFORMATION: Light chain

<400> SEQUENCE: 12

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
            85                  90                  95

Thr His Val Pro Tyr Thr Phe Gly Gly Gly Thr Lys Val Glu Ile Lys
        100                 105                 110

Arg Thr Val Ala Ala Pro Ser Val Phe Ile Phe Pro Pro Ser Asp Glu
    115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
210                 215

<210> SEQ ID NO 13
<211> LENGTH: 326
<212> TYPE: PRT
<213> ORGANISM: Artificial Sequence
```

<220> FEATURE:
<223> OTHER INFORMATION: Light chain

<400> SEQUENCE: 13

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
            100                 105                 110

Gly Thr Gly Gly Gly Ser Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Ser Val Phe Pro Leu Ala Pro Ser Ser Lys Ser Thr
225                 230                 235                 240

Ser Gly Gly Thr Ala Ala Leu Gly Cys Leu Val Lys Asp Tyr Phe Pro
                245                 250                 255

Ser Asp Ile Ala Val Glu Trp Glu Ser Gly Ala Leu Thr Ser Gly Val
            260                 265                 270

His Thr Phe Pro Ala Val Leu Gln Ser Ser Gly Leu Tyr Ser Leu Ser
        275                 280                 285

Ser Val Val Thr Val Pro Ser Ser Ser Leu Gly Thr Gln Thr Tyr Ser
    290                 295                 300

Cys Ser Val Met His Glu Ala Leu His Asn His Tyr Thr Gln Lys Ser
305                 310                 315                 320

Val Glu Pro Lys Ser Cys
                325

<210> SEQ ID NO 14
<211> LENGTH: 112
<212> TYPE: PRT
<213> ORGANISM: Artificial Sequence
<220> FEATURE:
<223> OTHER INFORMATION: VL

<400> SEQUENCE: 14

Asp Val Gln Met Thr Gln Ser Pro Ser Ser Leu Ser Ala Ser Val Gly

```
              1               5                  10                  15
            Asp Arg Val Thr Ile Thr Cys Arg Ser Ser Gln Ser Leu Leu His Ser
                            20                  25                  30

Asn Gly Asn Thr Tyr Leu His Trp Tyr Gln Gln Lys Pro Gly Lys Ala
                        35                  40                  45

Pro Lys Leu Leu Ile Tyr Thr Val Ser Asn Arg Phe Ser Gly Val Pro
                    50                  55                  60

Ser Arg Phe Ser Gly Ser Gly Ser Gly Thr Asp Phe Thr Leu Thr Ile
            65                  70                  75                  80

Ser Ser Leu Gln Pro Glu Asp Phe Ala Thr Tyr Tyr Cys Ser Gln Ser
                            85                  90                  95

Thr His Val Pro Tyr Thr Phe Gly Gly Gly Thr Lys Val Glu Ile Lys
                        100                 105                 110

<210> SEQ ID NO 15
<211> LENGTH: 7
<212> TYPE: PRT
<213> ORGANISM: Artificial Sequence
<220> FEATURE:
<223> OTHER INFORMATION: Linker

<400> SEQUENCE: 15

Gly Thr Gly Gly Gly Ser Gly
1               5

<210> SEQ ID NO 16
<211> LENGTH: 103
<212> TYPE: PRT
<213> ORGANISM: Artificial Sequence
<220> FEATURE:
<223> OTHER INFORMATION: CH2

<400> SEQUENCE: 16

Pro Ser Val Phe Leu Phe Pro Pro Lys Pro Lys Asp Thr Leu Met Ile
1               5                  10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Gly Leu Pro Ser Ser Ile Glu
                85                  90                  95

Lys Thr Ile Ser Lys Ala Lys
            100

<210> SEQ ID NO 17
<211> LENGTH: 104
<212> TYPE: PRT
<213> ORGANISM: Artificial Sequence
<220> FEATURE:
<223> OTHER INFORMATION: CH31

<400> SEQUENCE: 17

Gly Gln Pro Arg Glu Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30
```

```
Phe Pro Ser Asp Ile Ala Val Glu Trp Glu Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65              70                  75                  80

Tyr Ser Cys Ser Val Met His Glu Ala Leu His Asn His Tyr Thr Gln
                85                  90                  95

Lys Ser Val Glu Pro Lys Ser Cys
                100
```

<210> SEQ ID NO 18
<211> LENGTH: 333
<212> TYPE: PRT
<213> ORGANISM: Artificial Sequence
<220> FEATURE:
<223> OTHER INFORMATION: Heavy chain

<400> SEQUENCE: 18

```
His Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
                35                  40                  45

Gly Glu Ile Val Pro Ser Gln Gly Glu Ala Lys Tyr Asn Asp Lys Phe
        50                  55                  60

Lys Ala Arg Val Thr Ile Thr Ala Asp Lys Ser Thr Ser Thr Ala Tyr
 65              70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
                100                 105                 110

Val Ser Ser Gly Thr Gly Gly Ser Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
                180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Ala
    210                 215                 220

Lys Gly Gln Pro Arg Glu Pro Ser Val Phe Ile Phe Pro Pro Ser Asp
225                 230                 235                 240

Glu Gln Leu Lys Ser Gly Thr Ala Ser Val Val Cys Leu Val Asn Asn
                245                 250                 255

Phe Tyr Pro Arg Asp Ile Ala Val Glu Trp Glu Val Asp Asn Ala Leu
                260                 265                 270

Gln Ser Gly Asn Ser Gln Glu Ser Val Thr Glu Gln Asp Ser Lys Asp
        275                 280                 285
```

```
Ser Thr Tyr Ser Leu Ser Ser Thr Leu Thr Leu Ser Lys Ala Asp Tyr
        290                 295                 300

Glu Lys His Lys Val Tyr Ser Cys Ser Val Met His Glu Ala Leu His
305                 310                 315                 320

Asn His Tyr Thr Gln Lys Ser Phe Asn Arg Gly Glu Cys
                325                 330
```

<210> SEQ ID NO 19
<211> LENGTH: 115
<212> TYPE: PRT
<213> ORGANISM: Artificial Sequence
<220> FEATURE:
<223> OTHER INFORMATION: VH

<400> SEQUENCE: 19

```
His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
                100                 105                 110

Val Ser Ser
        115
```

<210> SEQ ID NO 20
<211> LENGTH: 108
<212> TYPE: PRT
<213> ORGANISM: Artificial Sequence
<220> FEATURE:
<223> OTHER INFORMATION: CH3k

<400> SEQUENCE: 20

```
Gly Gln Pro Arg Glu Pro Ser Val Phe Ile Phe Pro Pro Ser Asp Glu
1               5                   10                  15

Gln Leu Lys Ser Gly Thr Ala Ser Val Val Cys Leu Val Asn Asn Phe
            20                  25                  30

Tyr Pro Arg Asp Ile Ala Val Glu Trp Glu Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ser Cys Ser Val Met His Glu Ala Leu His Asn
                85                  90                  95

His Tyr Thr Gln Lys Ser Phe Asn Arg Gly Glu Cys
                100                 105
```

<210> SEQ ID NO 21
<211> LENGTH: 978
<212> TYPE: DNA

<213> ORGANISM: Artificial Sequence
<220> FEATURE:
<223> OTHER INFORMATION: Light chain

<400> SEQUENCE: 21

```
gatgtgcaga tgacccagag ccccagcagc ctgtctgcca gcgtgggcga cagagtgacc       60
atcacctgtc ggagcagcca gagcctgctg cacagcaacg gcaacaccta cctgcattgg      120
tatcagcaga agcccggcaa ggcccccaag ctgctgatct acaccgtgtc caacagattc      180
agcggcgtgc cctctagatt ctccggctct ggcagcggca ccgacttcac cctgaccatc      240
tctagcctgc agcccgagga cttcgccacc tactactgca gccagtccac ccacgtgccg      300
tatacctttg gcggaggcac caaggtggaa atcaaaggta ccggcggagg atctggccct      360
agcgtgttcc tgttcccccc aaagcccaag gacaccctga tgatctcccg gacccccgaa      420
gtgacctgcg tggtggtgga tgtgtcccac gaggaccctg aagtgaagtt taattggtac      480
gtggacggcg tggaagtgca taacgccaag accaagccca gaggaacag tacaacagc        540 acctaccggg tggtgtccgt gctgaccgtg ctgcaccagg actggctgaa cggcaaagag      600
tacaagtgca aggtgtccaa caagggcctg cccagcagca tcgagaaaac catcagcaag      660
gccaagggcc agcctcggga accctccgtg tttcctctgg cccctagcag aagagcacc       720 tctggcggaa cagccgccct gggctgcctc gtgaaggact acttccccag cgacattgcc      780
gtggaatggg agtctggcgc cctgaccagc ggagtgcata cctttccagc agtgctccag      840
agcagcggcc tgtacagcct gagcagcgtc gtgacagtgc ccagctctag cctgggcacc      900
cagacctact cttgcagcgt gatgcacgag gccctgcaca accactacac ccagaaaagc      960
gtggaaccca agagctgc                                                    978
```

<210> SEQ ID NO 22
<211> LENGTH: 999
<212> TYPE: DNA
<213> ORGANISM: Artificial Sequence
<220> FEATURE:
<223> OTHER INFORMATION: Heavy chain

<400> SEQUENCE: 22

```
cacgtgcagc tggtgcagtc tggcgccgaa gtgaagaaac ccggcagcag cgtgaaggtg       60
tcctgcaagg ccagcggcta caccttcacc gacttctaca tcaactgggt gcgccaggct      120
ccaggacagg gcctggaatg gatcggcgag atcgtgccta gcagggcga ggccaagtac       180 aacgacaagt tcaaggccag agtgaccatc accgccgaca agagcaccag caccgcctac      240
atggaactga gcagcctgcg gagcgaggac accgccgtgt actactgcgc cagatgggac      300
ttcctggact actggggcca gggcaccacc gtgacagtct cgagcggtac cggcggagga      360
tctggcccta gcgtgttcct gttccccccca aagcccaagg acaccctgat gatcagccgg      420 accccccgaag tgacctgcgt ggtggtggat gtgtcccacg aggaccctga agtgaagttc      480
aattggtacg tggacggcgt ggaagtgcac aacgccaaga ccaagcccag agaggaacag      540
tacaacagca cctaccgggt ggtgtccgtg ctgaccgtgc tgcaccagga ctggctgaac      600
ggcaaagagt acaagtgcaa ggtgtccaac aagggcctgc ccagcagcat cgagaaaacc      660
atcagcaagg ccaagggcca gcctcgggaa cccagcgtgt catcttccc acctccgac        720 gagcagctga gtctggcac agccagcgtc gtgtgcctcg tgaacaactt ctaccccaga       780
gacattgccg tggaatggga gtggacaac gccctccaga gcggcaacag ccaggaaagc      840
gtgaccgagc aggacagcaa ggactccacc tacagcctga gcagcaccct gaccctgagc      900
```

```
aaggccgact acgagaaaca taaggtgtac agctgctccg tgatgcacga ggccctgcac    960
aaccactaca cccagaagtc cttcaaccgg ggcgagtgc                           999
```

<210> SEQ ID NO 23
<211> LENGTH: 5
<212> TYPE: PRT
<213> ORGANISM: Artificial Sequence
<220> FEATURE:
<223> OTHER INFORMATION: CDR

<400> SEQUENCE: 23

Asp Phe Tyr Ile Asn
1               5

<210> SEQ ID NO 24
<211> LENGTH: 17
<212> TYPE: PRT
<213> ORGANISM: Artificial Sequence
<220> FEATURE:
<223> OTHER INFORMATION: CDR

<400> SEQUENCE: 24

Glu Ile Tyr Pro Tyr Ser Gly His Ala Tyr Tyr Asn Glu Lys Phe Lys
1               5                   10                  15

Ala

<210> SEQ ID NO 25
<211> LENGTH: 6
<212> TYPE: PRT
<213> ORGANISM: Artificial Sequence
<220> FEATURE:
<223> OTHER INFORMATION: CDR

<400> SEQUENCE: 25

Trp Asp Phe Leu Asp Tyr
1               5

<210> SEQ ID NO 26
<211> LENGTH: 16
<212> TYPE: PRT
<213> ORGANISM: Artificial Sequence
<220> FEATURE:
<223> OTHER INFORMATION: CDR

<400> SEQUENCE: 26

Arg Ser Ser Gln Ser Leu Leu His Ser Asn Gly Asn Thr Tyr Leu His
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: CDR

<400> SEQUENCE: 27

Thr Val Ser Asn Arg Phe Ser
1               5

<210> SEQ ID NO 28
<211> LENGTH: 9
<212> TYPE: PRT
<213> ORGANISM: Artificial Sequence
<220> FEATURE:
<223> OTHER INFORMATION: CDR

<400> SEQUENCE: 28

Ser Gln Ser Thr His Val Pro Tyr Thr
1               5

<210> SEQ ID NO 29
<211> LENGTH: 115
<212> TYPE: PRT
<213> ORGANISM: Artificial Sequence
<220> FEATURE:
<223> OTHER INFORMATION: VH

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
            35                  40                  45

Gly Glu Ile Tyr Pro Tyr Ser Gly His Ala Tyr Tyr Asn Glu Lys Phe
        50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser
        115

<210> SEQ ID NO 30
<211> LENGTH: 113
<212> TYPE: PRT
<213> ORGANISM: Artificial Sequence
<220> FEATURE:
<223> OTHER INFORMATION: VL

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg

<210> SEQ ID NO 31
<211> LENGTH: 223
<212> TYPE: PRT
<213> ORGANISM: Homo sapiens -continued

<400> SEQUENCE: 31

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 32
<211> LENGTH: 455
<212> TYPE: PRT
<213> ORGANISM: Homo sapiens

<400> SEQUENCE: 32

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140
```

-continued

```
Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 33
<211> LENGTH: 17
<212> TYPE: PRT
<213> ORGANISM: Homo sapiens

<400> SEQUENCE: 33

Asp Lys Thr His Thr Cys Pro Pro Cys Pro Ala Pro Glu Leu Leu Gly
1               5                   10                  15

Gly
```